(12) United States Patent
Igawa et al.

(10) Patent No.: US 8,384,286 B2
(45) Date of Patent: *Feb. 26, 2013

(54) COMPOUND AND ORGANIC LIGHT EMITTING DEVICE USING THE COMPOUND

(75) Inventors: Satoshi Igawa, Fujisawa (JP); Shinjiro Okada, Kamakura (JP); Jun Kamatani, Tokyo (JP); Naoki Yamada, Inagi (JP); Masashi Hashimoto, Tokyo (JP); Keiji Okinaka, Kawasaki (JP); Chika Nishi, Yokosuka (JP); Akihito Saitoh, Yokohama (JP); Takao Takiguchi, Chofu (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,149

(22) Filed: Nov. 3, 2011

(65) Prior Publication Data

US 2012/0043535 A1      Feb. 23, 2012

Related U.S. Application Data

(63) Continuation of application No. 12/295,240, filed as application No. PCT/JP2007/055583 on Mar. 13, 2007, now Pat. No. 8,072,136.

(30) Foreign Application Priority Data

Mar. 31, 2006  (JP) .................................. 2006-099896
Dec. 12, 2006  (JP) .................................. 2006-334985

(51) Int. Cl.
   *H01L 51/54* (2006.01)
(52) U.S. Cl. ............. 313/504; 257/40; 585/22; 428/690
(58) Field of Classification Search .................. None
   See application file for complete search history.

(56) References Cited

U.S. PATENT DOCUMENTS 7,049,011 B2    5/2006   Ebisawa et al.
(Continued)

FOREIGN PATENT DOCUMENTS

EP           1 380 556 A1      1/2004
(Continued)

OTHER PUBLICATIONS

Supplementary European Search Report for EP Application No. 07 73 9026 (1pg).
(Continued)

*Primary Examiner* — Jennifer Chriss
*Assistant Examiner* — J. L. Yang
(74) *Attorney, Agent, or Firm* — Fitzpatrick, Cella, Harper & Scinto

(57) ABSTRACT

A novel mono(benzo[k]fluoranthene) compound having a molecular structure containing at least one condensed ring aromatic group which is tricyclic or more at any of 7- to 9-positions of benzo[k]fluoranthene. Also an organic light emitting device including at least a pair of electrodes formed of an anode and a cathode, and a layer formed of an organic compound, the layer being interposed between the pair of electrodes, in which the layer formed of an organic compound contains a compound represented by the following structural formula. An organic light emitting device in which the layer is a light emitting layer.

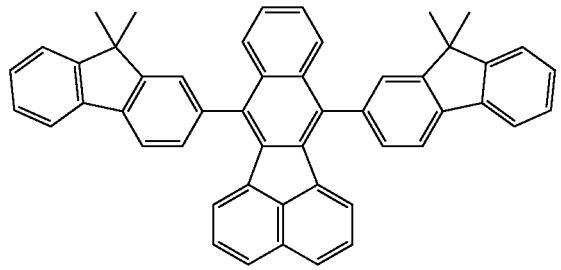

8 Claims, 6 Drawing Sheets

U.S. PATENT DOCUMENTS

| | | | |
|---|---|---|---|
| 7,097,917 | B1 | 8/2006 | Fujita et al. |
| 7,977,869 | B2 * | 7/2011 | Saitoh et al. ............... 313/504 |
| 8,072,136 | B2 * | 12/2011 | Igawa et al. ............... 313/504 |
| 2007/0252141 | A1 | 11/2007 | Negishi et al. |
| 2008/0272692 | A1 | 11/2008 | Hashimoto et al. |
| 2009/0102371 | A1 | 4/2009 | Hashimoto et al. |
| 2009/0278118 | A1 | 11/2009 | Ohrui et al. |
| 2009/0278447 | A1 | 11/2009 | Saitoh et al. |

FOREIGN PATENT DOCUMENTS

| | | |
|---|---|---|
| JP | 10-189247 A | 7/1998 |
| JP | 2000-007587 A | 1/2000 |
| JP | 2000-007594 A | 1/2000 |
| JP | 2003-026616 A | 1/2003 |
| JP | 2005068087 A | 3/2005 |
| JP | 2005-235787 A | 9/2005 |
| KR | 2003-0009541 A | 1/2003 |
| WO | 02/085822 A1 | 10/2002 |

OTHER PUBLICATIONS

Taylor et al., "Formation of C60 by Pyrolysis of Naphthalene," 366 (23) Nature 728-31 (Dec. 1993).

Mallakpour et al., "A Convenient One-Step Synthesis of Dialykylbenzo[k]fluoranthenes and Tetraethylbisbenzo[k][k]Fluoranthenes", 28(6) Organic Preparations and Procedures International 691-93 (1996).

Mallakpour et al., "Reaction of 3,4,3',4'-tetradehydrobiphenyl (Bisbenzyne) with Tetracyclone and Acecyclone", 39B(3) Indian Journal of Chemistry, Section B: Organic Chemistry Including Medicinal Chemistry 173-76 (Mar. 2000).

Korean Office Action issued in corresponding Korean application No. 10-2008-7026743 dated Aug. 24, 2010—6 pages.

Machine Translation of JP 2005068087A (2010).

* cited by examiner

COMPOUND AND ORGANIC LIGHT EMITTING DEVICE USING THE COMPOUND

This application is a continuation of application Ser. No. 12/295,240, filed Sep. 29, 2008, which is a national phase application based on PCT/JP2007/055583, filed Mar. 13, 2007, the entire disclosure of each of which is incorporated herein by reference.

TECHNICAL FIELD

The present invention relates to a novel compound and an organic light emitting device using the compound, and more specifically, to an organic light emitting device using the novel compound in its light emitting layer.

BACKGROUND ART

An organic light emitting device includes: an anode; a cathode; and a thin film containing a fluorescent organic compound or a phosphorescent organic compound, the thin film being interposed between the anode and the cathode. An electron and a hole are injected from the respective electrodes. As a result, the organic light emitting device generates an exciton of the fluorescent organic compound or of the phosphorescent organic compound. The device utilizes light to be radiated when the exciton returns to its ground state. Recent progress in an organic light emitting device is remarkable. The organic light emitting device has such characteristics that it can be turned into a thin, lightweight light emitting device which: provides high luminance at a low applied voltage; and has the diversity of a luminous wavelength and high-speed responsiveness. The characteristics suggest that the light emitting device may be used in a wide variety of applications.

However, the conventional organic light emitting device requires optical output with additionally higher luminance or higher conversion efficiency. In addition, the organic light emitting device still involves many problems in terms of durability such as a change with time due to long-term use and deterioration due to, for example, an atmospheric gas containing oxygen or humidity. Further, when it is attempted that the device is applied to a full-color display and the like, each of blue light, green light, and red light must be emitted at a good color purity. However, problems concerning the emission have not been sufficiently solved yet.

In addition, examples of a patent document describing a compound having a benzo[k]fluoranthene skeleton include Japanese Patent Application Laid-Open Nos. H10-189247, 2005-235787, 2000-007587, 2000-007594 and 2005-068087.

DISCLOSURE OF THE INVENTION

An object of the present invention is to provide a novel mono(benzo[k]fluoranthene) compound formed of a molecular structure containing at least one condensed ring aromatic group which is tricyclic or more at any of 7- to 9-positions of benzo[k]fluoranthene.

Another object of the present invention is to provide an organic light emitting device which uses the above compound and which has an optical output with extremely high efficiency and extremely high brightness. Another object of the present invention is to provide an organic light emitting device having extremely high durability. Another object of the present invention is to provide an organic light emitting device which can be easily produced at a relatively low cost.

According to the present invention, there is provided a mono(benzo[k]fluoranthene) compound represented by the following general formula (I):

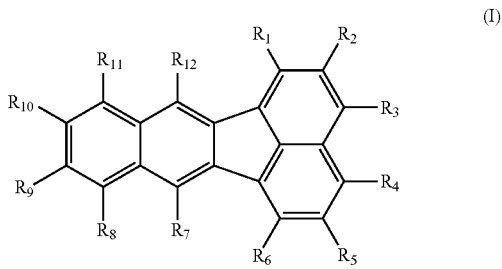

where $R_1$ to $R_{12}$ each represent a hydrogen atom, a linear or branched alkyl group, a substituted or unsubstituted aryl group, or a substituted or unsubstituted heterocyclic group, provided that at least one of $R_7$, $R_8$, and $R_9$ represents a substituted or unsubstituted condensed ring aromatic group which is tricyclic or more.

Further, according to the present invention, there is provided a mono(benzo[k]fluoranthene) compound, in which one or more of $R_{10}$, $R_{11}$, and $R_{12}$ in the general formula (I) each represent a substituted or unsubstituted aryl group, or a substituted or unsubstituted heterocyclic group.

Further, according to the present invention, there is provided a mono(benzo[k]fluoranthene) compound, in which one or more of $R_{10}$, $R_{11}$, and $R_{12}$ in the general formula (I) each represent a substituted or unsubstituted condensed ring aromatic group which is tricyclic or more.

Further, according to the present invention, there is provided a mono(benzo[k]fluoranthene) compound, in which $R_7$ in the general formula (I) represents a substituted or unsubstituted fluorenyl group.

Further, according to the present invention, there is provided a mono(benzo[k]fluoranthene) compound which is represented by the following general formula (II):

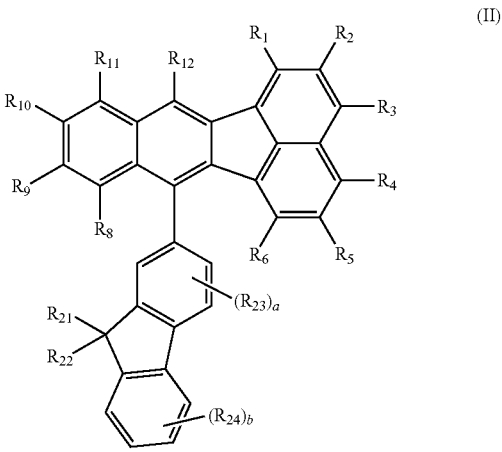

where:
$R_1$ to $R_6$, and $R_8$ to $R_{12}$ each represent a hydrogen atom, a linear or branched alkyl group, a substituted or unsubstituted aryl group, or a substituted or unsubstituted heterocyclic group; and $R_{21}$ and $R_{22}$ each represent a hydrogen atom, an alkyl group, a substituted or unsubstituted aryl group, or a substituted or unsubstituted heterocyclic group, and $R_{21}$ and $R_{22}$ may be identical to or different from each other; $R_{23}$ and $R_{24}$ each represent a hydrogen atom, an alkyl group, a substituted or unsubstituted aryl group, a substituted or unsubstituted heterocyclic group, a substituted amino group, or a halogen atom; a represents an integer of 1 to 3, and b represents an integer of 1 to 4; and, when the number of any one of $R_{23}$ and $R_{24}$ is two or more, $R_{23}$'s or $R_{24}$'s may be identical to or different from each other.

Further, according to the present invention, there is provided a mono(benzo[k]fluoranthene) compound, in which the mono(benzo[k]fluoranthene) compound is represented by the following general formula (III):

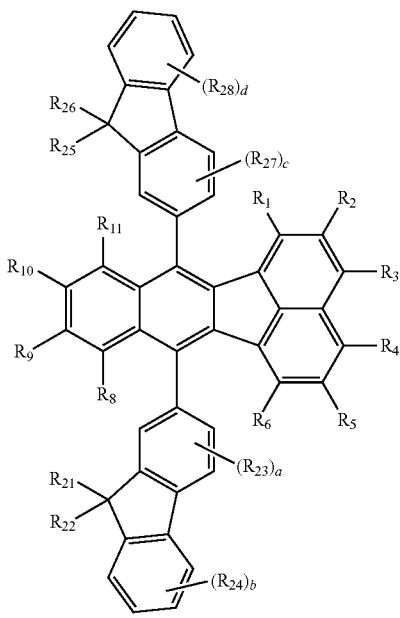

(III)

where:

$R_1$ to $R_6$, and $R_6$ to $R_{11}$ each represent a hydrogen atom, a linear or branched alkyl group, a substituted or unsubstituted aryl group, or a substituted or unsubstituted heterocyclic group; and $R_{21}$, $R_{22}$, $R_{25}$, and $R_{26}$ each represent a hydrogen atom, an alkyl group, a substituted or unsubstituted aryl group, or a substituted or unsubstituted heterocyclic group, and $R_{21}$, $R_{22}$, $R_{25}$, and $R_{26}$ may be identical to or different from each other; $R_{23}$, $R_{24}$, $R_{27}$, and $R_{28}$ each represent a hydrogen atom, an alkyl group, a substituted or unsubstituted aryl group, a substituted or unsubstituted heterocyclic group, a substituted amino group, or a halogen atom; a and c each represent an integer of 1 to 3, and b and d each represent an integer of 1 to 4, and, when the number of any one of $R_{23}$, $R_{24}$, $R_{27}$, and $R_{28}$ is two or more, $R_{23}$'s, $R_{24}$'s, $R_{27}$'s, and $R_{28}$'s may be identical to or different from each other.

Further, according to the present invention, there is provided a mono(benzo[k]fluoranthene) compound, in which $R_7$ in the general formula (I) represents a substituted or unsubstituted fluoranthenyl group.

Further, according to the present invention, there is provided a mono(benzo[k]fluoranthene) compound which is represented by the following general formula (IV):

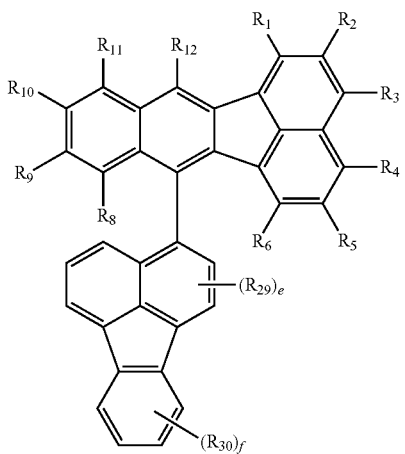

(IV)

where:

$R_1$ to $R_6$, and $R_8$ to $R_{12}$ each represent a hydrogen atom, a linear or branched alkyl group, a substituted or unsubstituted aryl group, or a substituted or unsubstituted heterocyclic group; and $R_{29}$ and $R_{30}$ each represent a hydrogen atom, an alkyl group, a substituted or unsubstituted aryl group, a substituted or unsubstituted heterocyclic group, a substituted amino group, or a halogen atom; e represents an integer of 1 to 5, and f represents an integer of 1 to 4; and, when the number of any one of $R_{29}$ and $R_{30}$ is two or more, $R_{29}$'s or $R_{30}$'s may be identical to or different from each other.

According to the present invention, there is provided a mono(benzo[k]fluoranthene) compound which is represented by the following general formula (V):

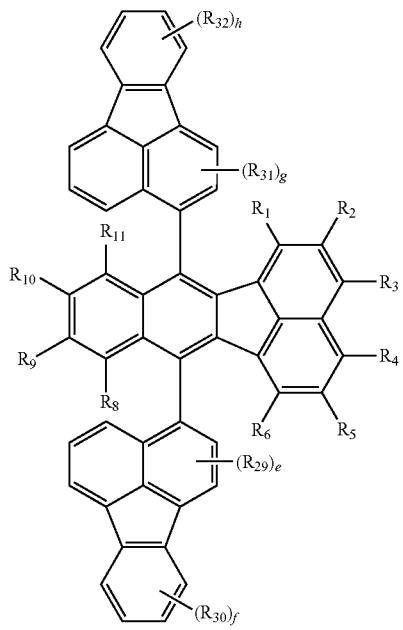

(V)

where:

$R_1$ to $R_6$, and $R_8$ to $R_{11}$ each represent a hydrogen atom, a linear or branched alkyl group, a substituted or unsubstituted aryl group, or a substituted or unsubstituted heterocyclic group; and $R_{29}$ to $R_{32}$ each represent a hydrogen atom, an alkyl group, a substituted or unsubstituted aryl group, a substituted or unsubstituted heterocyclic group, a substituted amino group, or a halogen atom; e and g each represent an integer of 1 to 5, and f and h each represent an integer of 1 to 4; and, when the number of any one of $R_{29}$, $R_{30}$, $R_{31}$, and $R_{32}$ is two or more, $R_{29}$'s, $R_{30}$'s, $R_{31}$'s, or $R_{32}$'s may be identical to or different from each other.

Specific examples of the substituents in the general formulae (I), (II), (III), (IV), and (V) are shown below; provided that the examples are merely representative examples, and the present invention is not limited to those examples.

As the alkyl group, there may be given a methyl group, an ethyl group, a normal propyl group, an isopropyl group, an normal butyl group, a tertiary butyl group, an octyl group, a cyclohexyl group, a trifluoromethyl group, and the like.

Examples of the aryl group include a phenyl group, a biphenyl group, a terphenyl group, a fluorenyl group, a naphtyl group, a fluoranthenyl group, an anthryl group, a phenanthryl group, a pyrenyl group, a tetracenyl group, a pentacenyl group, a triphenylenyl group, and a perylenyl group.

As the heterocyclic group, there may be given a thienyl group, a pyrrolyl group, a pyridyl group, an oxazolyl group, an oxadiazolyl group, a thiazolyl group, a thiadiazolyl group, and the like.

As the substituted amino group, there may be given a dimethylamino group, a diethylamino group, a dibenzylamino group, a diphenylamino group, a ditolylamino group, a dianisolylamino group, and the like. As the halogen atom, there may be given fluorine, chlorine, bromine, iodine, and the like.

Examples of a condensed ring aromatic group which is tricyclic or more include a fluorenyl group, a pyrenyl group, a fluoranthenyl group, a benzofluoranthenyl group, a tetracenyl group, a pentacenyl group, a triphenylenyl group, a perylenyl group, and a chrysenyl group.

Examples of a condensed ring aromatic skeleton which is tetracyclic or more include a pyrene skeleton, a fluoranthene skeleton, a benzofluoranthene skeleton, a tetracene skeleton, a triphenylene skeleton, and a chrysene skeleton.

Examples of substituents which the above-mentioned substituents may have include: alkyl groups such as a methyl group, an ethyl group, and a propyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; and halogen atoms such as fluorine, chlorine, bromine, and iodine.

Further, according to the present invention, there is provided an organic light emitting device including: a pair of electrodes formed of an anode and a cathode; and an organic compound layer being interposed between the pair of electrodes, in which the organic compound layer contains at least one kind of compound represented by the above-mentioned general formula (I).

Further, according to the present invention, there is provided an organic light emitting device in which the organic compound layer is a light emitting layer. Further, according to the present invention, there is provided an organic light emitting device in which the light emitting layer is formed of at least two kinds of compounds including a host and a guest.

In addition, according to the present invention, there is provided an organic light emitting device including: a pair of electrodes formed of an anode and a cathode; and an organic compound layer placed between the pair of electrodes, in which the organic compound layer contains a first compound having a benzo[k]fluoranthene skeleton and a second compound having a condensed ring aromatic skeleton which is tetracyclic or more, the second compound having an energy gap larger than that of the first compound.

Further, there is provided an organic light emitting device, in which the condensed ring aromatic skeleton which is tetracyclic or more is one of a pyrene skeleton and a fluoranthene skeleton.

Further, there is provided an organic light emitting device, in which the first compound is a mono(benzo[k]fluoranthene) compound represented by the general formula (I).

Further, there is provided an organic light emitting device, in which the first compound and the second compound have the same condensed ring aromatic skeleton.

Further, there is provided an organic light emitting device, in which the condensed ring aromatic skeleton includes a fluorene skeleton.

Further, there is provided an organic light emitting device, in which the organic light emitting device includes an electroluminescence device that emits light by applying a voltage between the pair of electrodes.

The compound of the present invention has a high glass transition temperature, and the light emitting device of the present invention using the compound of the present invention as a host or guest for its light emitting layer can realize highly efficient light emission with good color purity. In addition, the device is an excellent device because the device has high heat stability, and keeps high brightness for a time period longer than that in the case where a conventionally used compound is used.

Further features of the present invention will become apparent from the following description of exemplary embodiments with reference to the attached drawings.

BEST MODE FOR CARRYING OUT THE INVENTION

Figure 1:
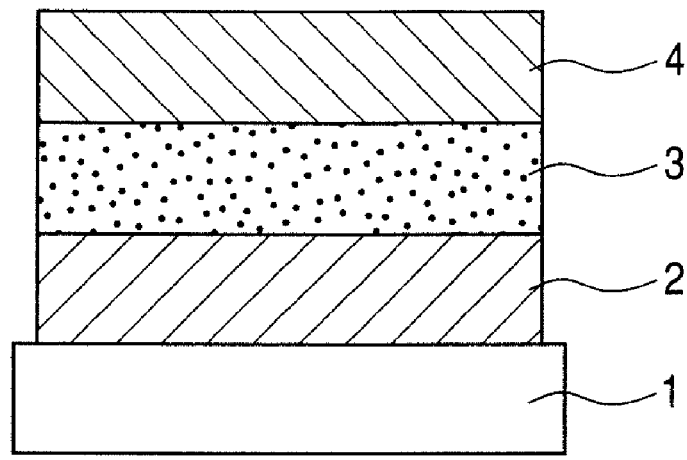
FIG. 1 is a sectional view showing an example of an organic light emitting device of the present invention.

Hereinafter, the present invention will be described in detail.

When a light emitting layer in an organic light emitting device is formed of a carrier transporting host material and a guest, a main process for light emission includes the following several steps:

1. the transport of an electron or a hole in the light emitting layer;
2. the generation of an exciton of the host material;
3. the transfer of excitation energy between host material molecules; and
4. the movement of the excitation energy from the host material to the guest.

Desired energy movement in each step, and light emission occur in competition with various deactivation steps.

Needless to say, the emission quantum yield of a light emission central material itself must be large in order that the luminous efficiency of an organic light emitting device may be improved. However, the efficiency with which energy movement between host and host molecules or between host and guest molecules can be performed is also of great concern. In addition, the deterioration of light emission due to energization is assumed to be related to a change in environment surrounding a light emitting material due to at least the light emission central material itself or a molecule around the light emission central material, though no causes for the deterioration have been revealed at present.

In view of the foregoing, the inventors of the present invention have made various studies. As a result, the inventors have found that a device using a compound represented by the general formula (I) as a host or guest for its light emitting layer emits light with high efficiency, keeps high brightness for a long time period, and shows small deterioration of light emission due to energization.

One possible cause for the deterioration of the light emission due to the energization may be the deterioration of the thin-film shape of the light emitting layer. The deterioration of the thin-film shape may result from the crystallization of the organic thin film due to, for example, the temperature of an environment in which the device is driven or heat generation at the time of the driving of the device. The crystallization may originate from the low glass transition temperature of a material for the thin film, so it is desired that an organic EL material have a high glass transition temperature. An improvement in durability of an organic light emitting device can be expected from the compound represented by the general formula (I) of the present invention because the compound has a high glass transition temperature.

The compound of the present invention will be described.

Benzo[k]fluoranthene is known to be a compound having a quantum yield of 1.0 in a dilute solution (J. Photochem. 18, 9-17 (1982)). However, the compound is extremely apt to undergo concentration quenching, and a benzo[k]fluoranthene thin film does not emit light. Accordingly, high efficiency may not be obtained from benzo[k]fluoranthene itself when benzo[k]fluoranthene is used in an organic EL device. In addition, benzo[k]fluoranthene contains a large amount of ultraviolet emission components each having a maximum luminous wavelength of 400 nm; the wavelength is not optimum enough to allow benzo[k]fluoranthene to be used as a blue light emitting material. When benzo[k]fluoranthene is used as a light emitting material in a light emitting device, the device is doped with the light emitting material at a relatively high concentration of about 0.1 to 20 wt % with respect to a host material. Accordingly, unlike a state where the concentration of the light emitting material is low, the light emitting properties of the light emitting material in a solid film are of extreme importance. In addition, a compound having a large amount of emission components each having a maximum luminous wavelength of 450 to 460 nm is expected to emit blue light with high efficiency and good color purity when the compound is used as a blue light emitting material for a display.

The compound of the present invention has one benzo[k]fluoranthene site in its molecule. Accordingly, the probability that benzo[k]fluoranthene sites collide with each other in the film of a light emitting device in which the compound is dispersed may be reduced, concentration quenching may be suppressed, and highly efficient light emission may be expected. Further, a relatively large, condensed ring aromatic group which is tricyclic or more is introduced into any of 7- to 9-positions of benzo[k]fluoranthene, so the suppression of concentration quenching may be expected owing to the steric hindrance of a substituent. Further, the presence of a substituted or unsubstituted aryl group or a substituted or unsubstituted heterocyclic group at any of 10- to 12-positions of benzo[k]fluoranthene may improve not only the ease with which the compound is synthesized but also the stability of the compound. In addition, a compound having a condensed ring aromatic group which is tricyclic or more at 7-position of benzo[k]fluoranthene is particularly preferable because a substituent may show large steric hindrance at 7-position of benzo[k]fluoranthene. A compound having a condensed ring aromatic group which is tricyclic or more at each of 7- and 12-positions of benzo[k]fluoranthene is also preferable because a substituent may similarly show large steric hindrance at 12-position of benzo[k]fluoranthene. In addition, from the viewpoint of a luminous wavelength, the lengthening of a wavelength can be expected from the property with which an electron is donated to benzo[k]fluoranthene. In addition, from the viewpoint of a quantum yield, a compound having, as a substituent, a condensed ring aromatic structure which is tricyclic or more and which has a large oscillator strength is preferable for the realization of a high quantum yield. In addition, among the condensed ring aromatic groups each of which is tricyclic or more, a fluorenyl group is a particularly preferable condensed ring aromatic group which is tricyclic or more because the group is expected to show steric hindrance by a substituent attached to the carbon atom at 9-position of the group. A fluoranthenyl group is also particularly preferable because of the following reason: when benzo[k]fluoranthene is substituted by the fluoranthenyl group having a skeleton similar to that of benzo[k]fluoranthene, the highest occupied molecular orbital (HOMO) and lowest unoccupied molecular orbital (LUMO) of a molecule of the resultant compound expand over the entirety of the molecule, so an improvement in stability of the molecule can be expected.

In addition, as described above, a compound to be used in an organic EL device is required to have a high glass transition temperature. In general, a material having a larger molecular weight has a higher glass transition temperature. When a substituent to be introduced into benzo[k]fluoranthene is limited to a small aromatic ring such as a phenyl group or a tolyl group, the resultant compound has a small molecular weight, so a high glass transition temperature may not be expected. In addition, the introduction of only an alkyl group may reduce the glass transition temperature of the resultant compound, though the introduction increases the molecular weight of the compound. Accordingly, as the substituent to be introduced into benzo[k]fluoranthene, the condensed ring aromatic group which is tricyclic or more used in the present invention is preferable from the viewpoint of a glass transition temperature.

Accordingly, the compound of the present invention is a compound represented by any one of the following general formulae (I) to (V).

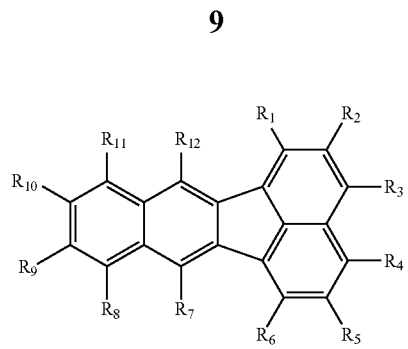
(I)

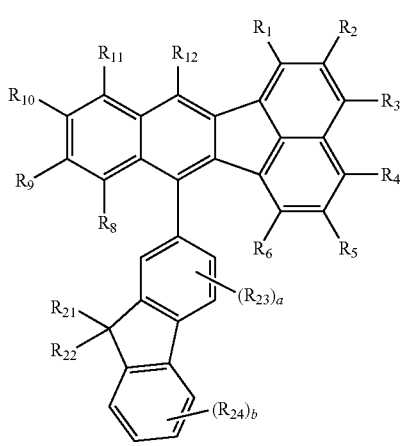
(II)

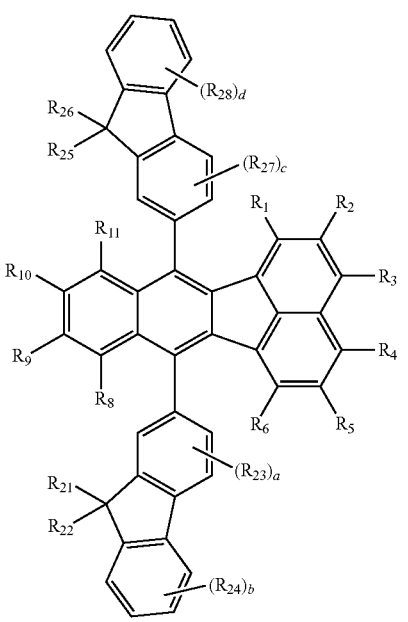
(III)

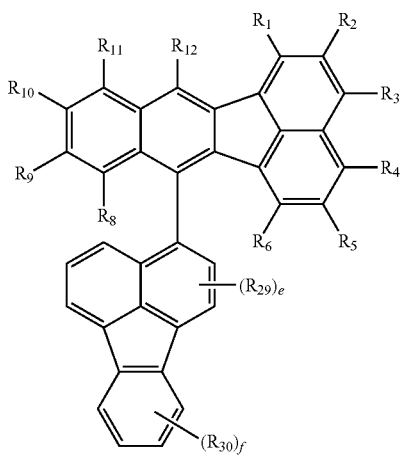
(IV)

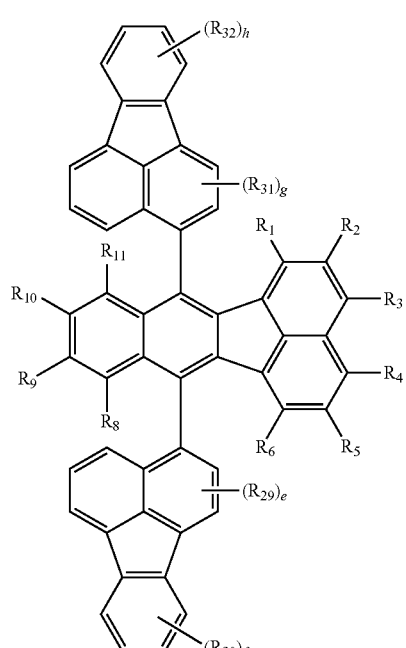
(V)

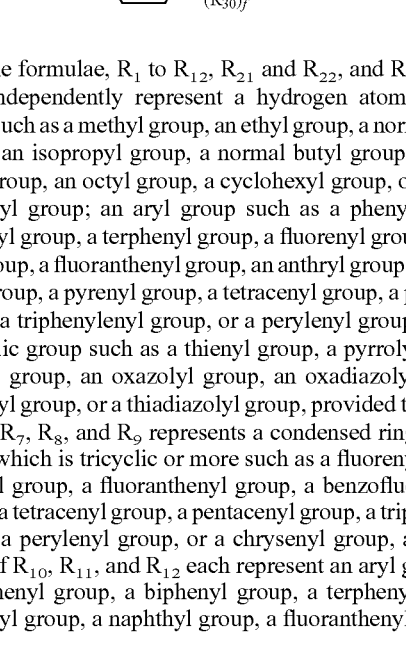

In the formulae, $R_1$ to $R_{12}$, $R_{21}$ and $R_{22}$, and $R_{25}$ and $R_{26}$ each independently represent a hydrogen atom; an alkyl group such as a methyl group, an ethyl group, a normal propyl group, an isopropyl group, a normal butyl group, a tertiary butyl group, an octyl group, a cyclohexyl group, or a trifluoromethyl group; an aryl group such as a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, or a perylenyl group; or a heterocyclic group such as a thienyl group, a pyrrolyl group, a pyridyl group, an oxazolyl group, an oxadiazolyl group, a thiazolyl group, or a thiadiazolyl group, provided that at least one of $R_7$, $R_8$, and $R_9$ represents a condensed ring aromatic group which is tricyclic or more such as a fluorenyl group, a pyrenyl group, a fluoranthenyl group, a benzofluoranthenyl group, a tetracenyl group, a pentacenyl group, a triphenylenyl group, a perylenyl group, or a chrysenyl group, and one or more of $R_{10}$, $R_{11}$, and $R_{12}$ each represent an aryl group such as a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, or a perylenyl group; or a heterocyclic group such as a thienyl group, a pyrrolyl group, a pyridyl group, an oxazolyl group, an oxadiazolyl group, a thiazolyl group, or a thiadiazolyl group.

$R_{21}$ and $R_{22}$, and $R_{25}$ and $R_{26}$ each preferably represent an alkyl group in terms of the stability of the carbon atom at 9-position of a fluorenyl group against a radical. In addition, an increase in the length of an alkyl chain at 9-position of the fluorenyl group may reduce the glass transition temperature. Accordingly, $R_{21}$ and $R_{22}$, and $R_{25}$ and $R_{26}$ each more preferably represent an alkyl group having a short carbon chain such as a methyl group or an ethyl group. In addition, $R_{21}$ and $R_{22}$, and $R_{25}$ and $R_{26}$, which may be identical to or different from one another, are preferably identical to one another from the viewpoint of the ease with which the compound is synthesized.

$R_{23}$ and $R_{24}$, $R_{27}$ and $R_{28}$, and $R_{29}$ to $R_{32}$ each represent a hydrogen atom, an alkyl group such as a methyl group, an ethyl group, a normal propyl group, an isopropyl group, a normal butyl group, a tertiary butyl group, an octyl group, a cyclohexyl group, or a trifluoromethyl group; an aryl group such as a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, or a perylenyl group; a heterocyclic group such as a thienyl group, a pyrrolyl group, a pyridyl group, an oxazolyl group, an oxadiazolyl group, a thiazolyl group, or a thiadiazolyl group; an amino group such as a dimethylamino group, a diethylamino group, a dibenzylamino group, a diphenylamino group, a ditolylamino group, or a dianisolylamino group; or a halogen atom such as fluorine, chlorine, bromine, or iodine. a and c each represent an integer of 1 to 3, b and d each represent an integer of 1 to 4, e and g each represent an integer of 1 to 5, and f and h each represent an integer of 1 to 4. When the number of any one of $R_{23}$ and $R_{24}$, $R_{27}$ and $R_{29}$, and $R_{29}$ to $R_{32}$ is two or more, $R_{23}$'s, $R_{24}$'s, $R_{27}$'s, $R_{28}$'s, $R_{29}$'s, $R_{30}$'s, $R_{31}$'s, or $R_{32}$'s may be identical to or different from each other.

Hereinafter, specific examples of the structural formula of an organic compound to be used in the present invention are shown below. It should be noted that the examples are merely representative examples, and the present invention is not limited to the examples.

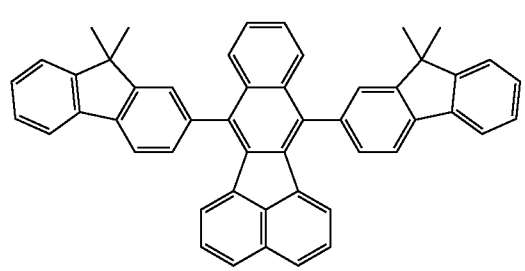

A-1

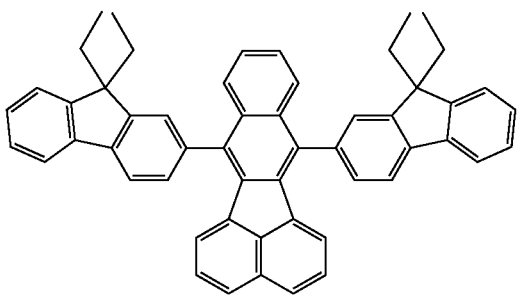

A-2

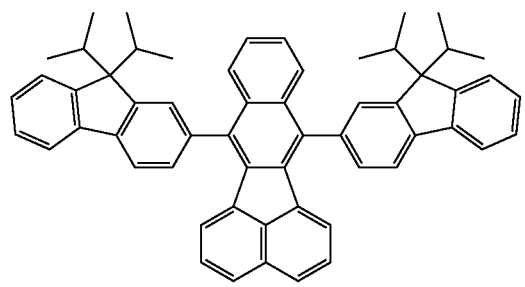

A-3

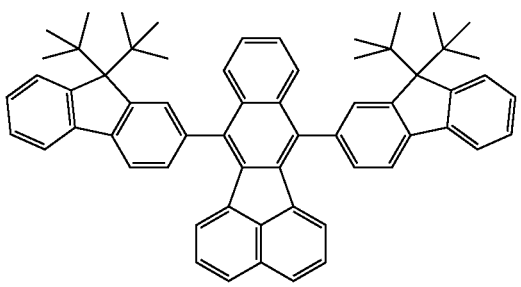

A-4

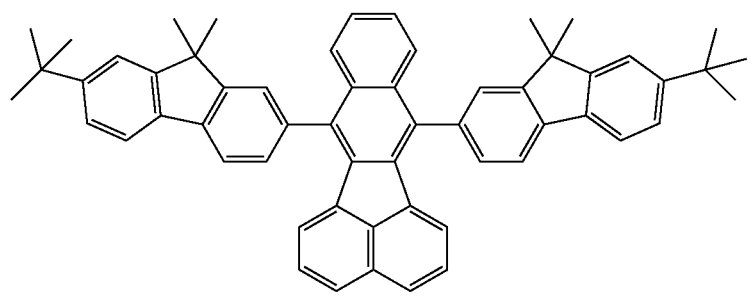

A-5

-continued
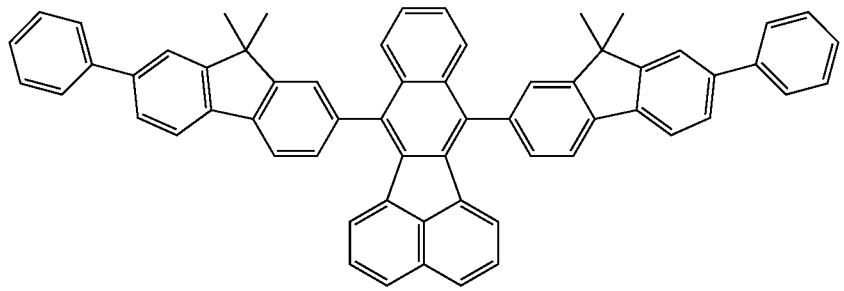
A-6
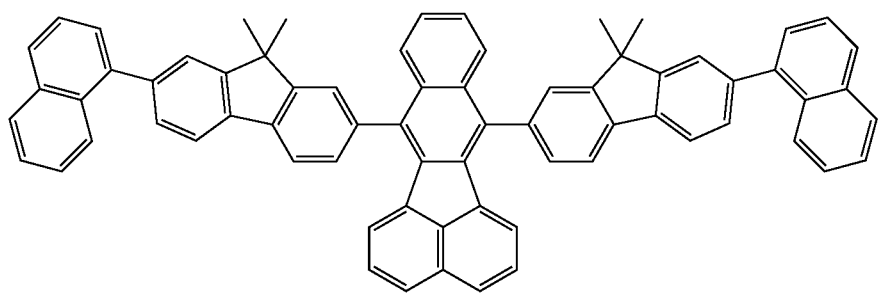
A-7
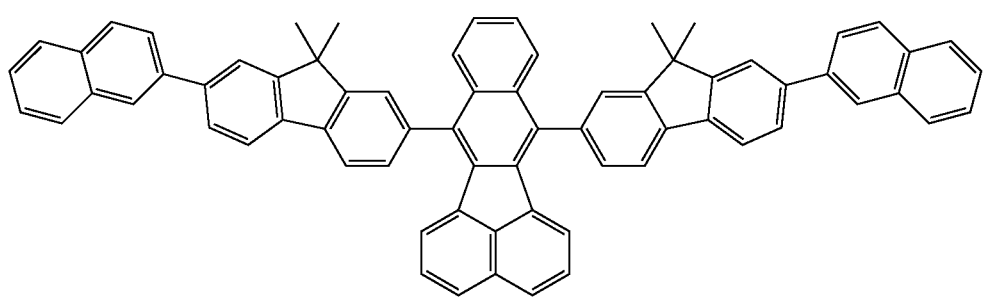
A-8
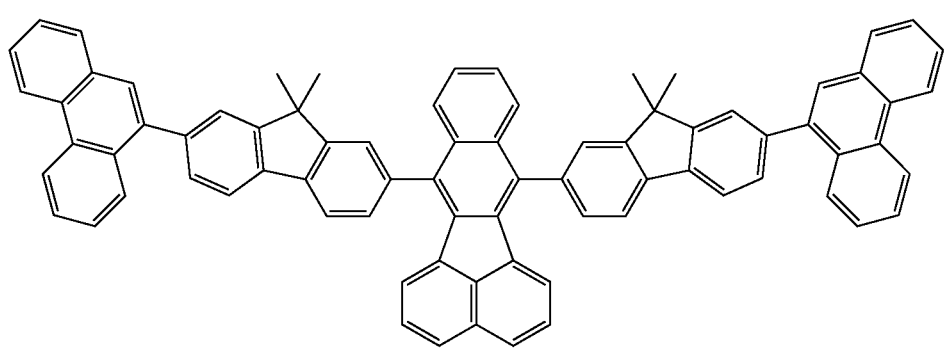
A-9
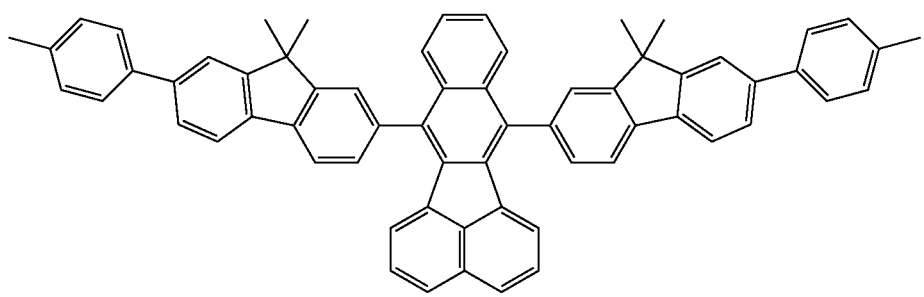
A-10

-continued
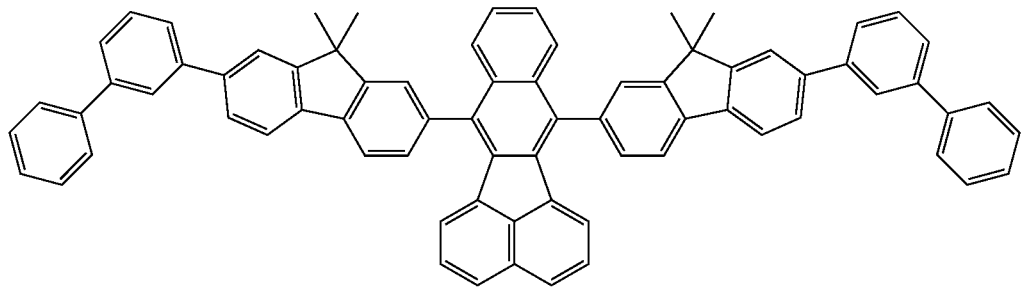
A-11
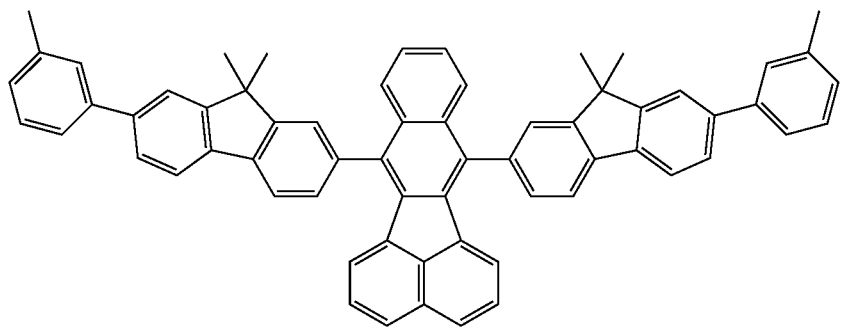
A-12
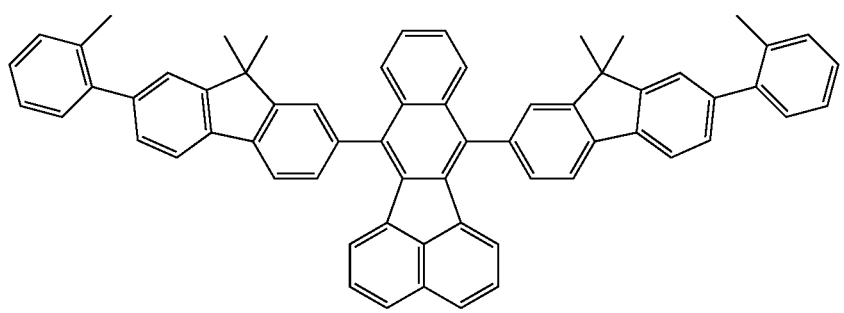
A-13
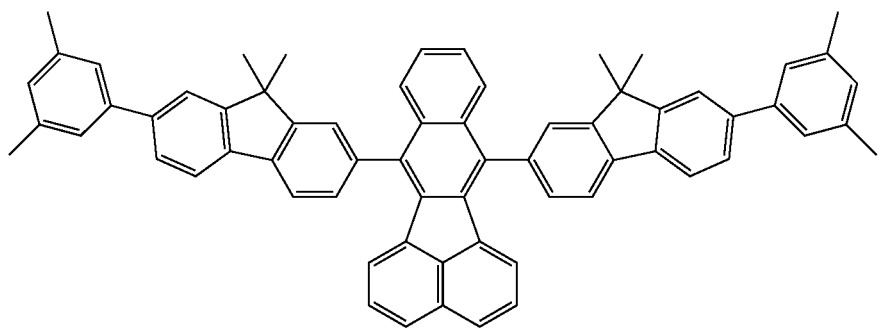
A-14
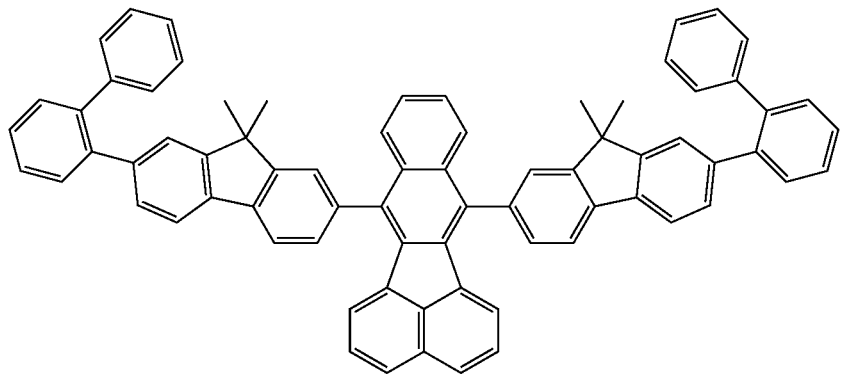
A-15

-continued
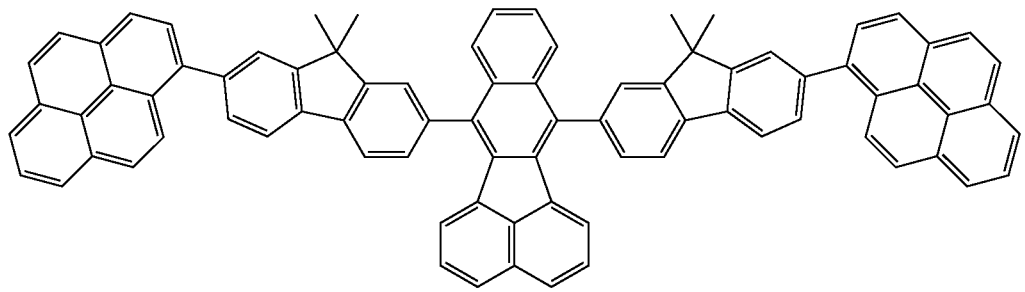
A-16
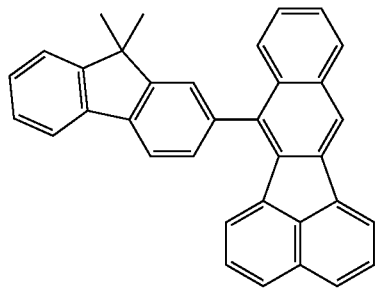
A-17
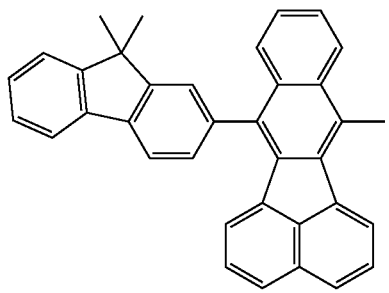
A-18
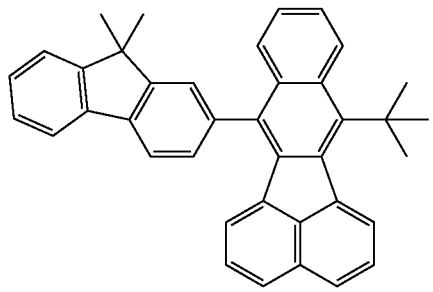
A-19
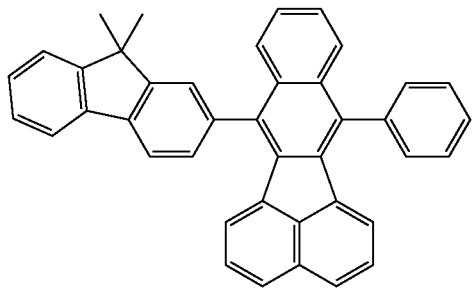
A-20
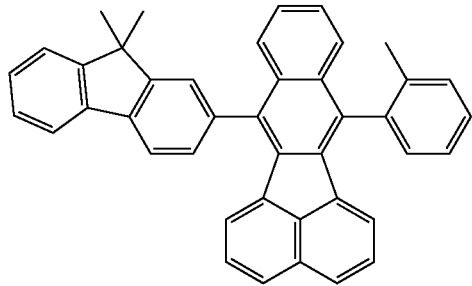
A-21
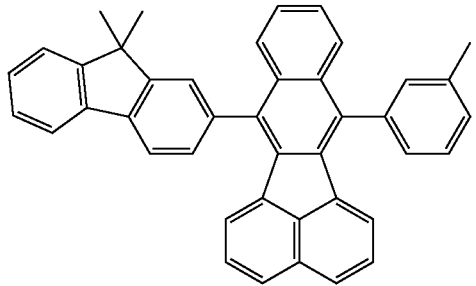
A-22
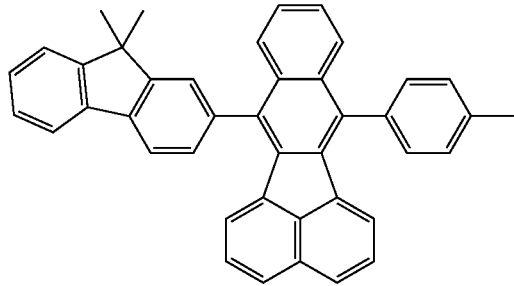
A-23
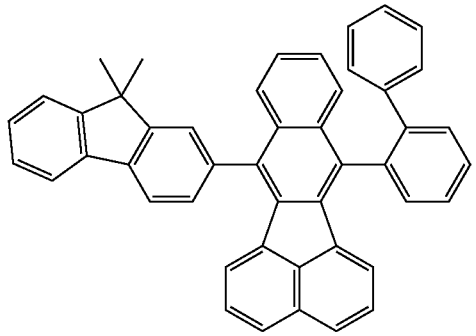
A-24

-continued
A-25
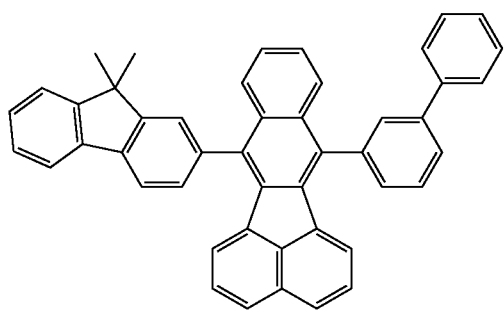
A-26
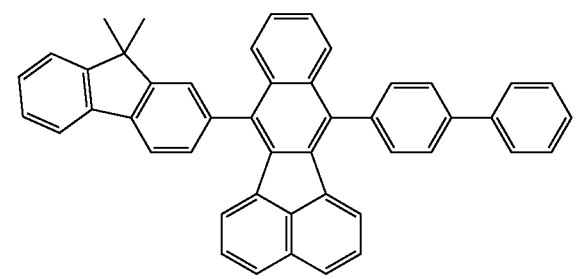
A-27
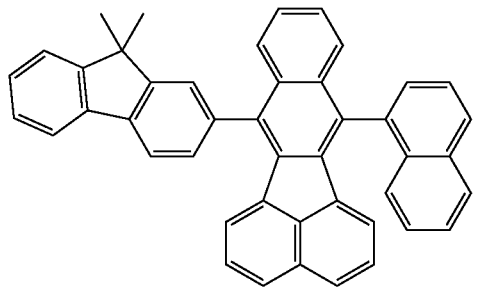
A-28
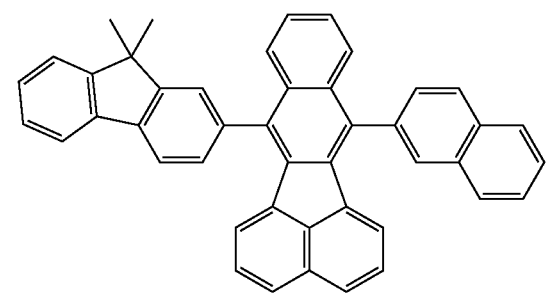
A-29
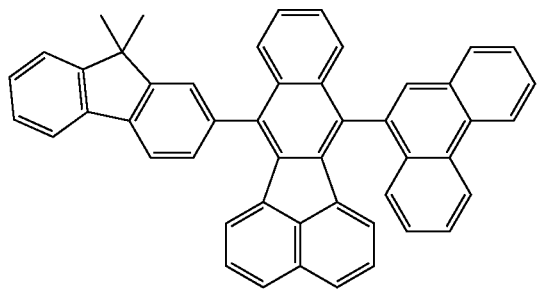
A-30
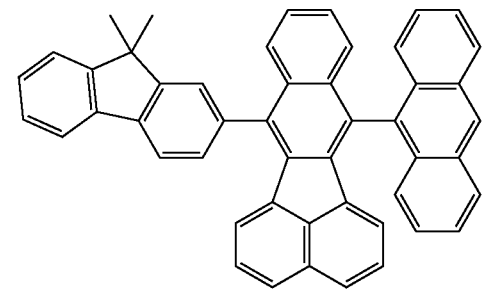
A-31
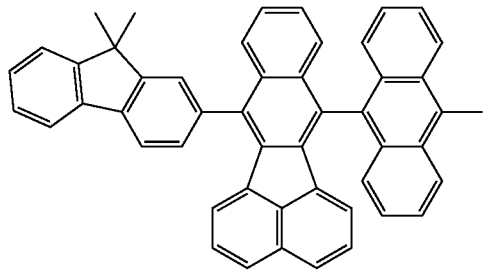
A-32
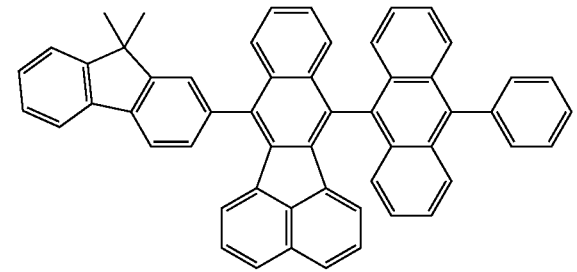
A-33
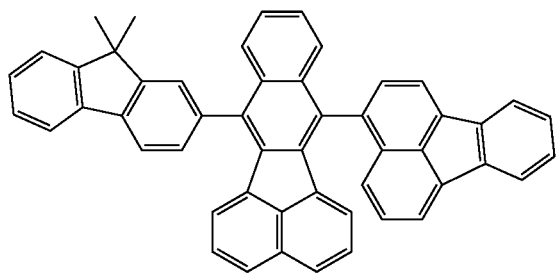
A-34
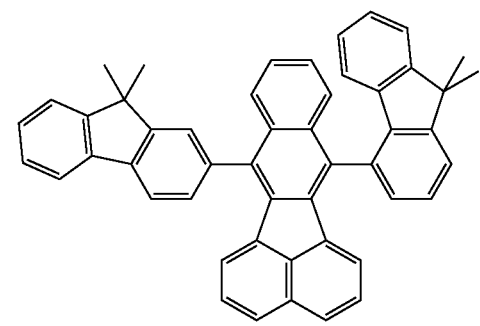

A-35
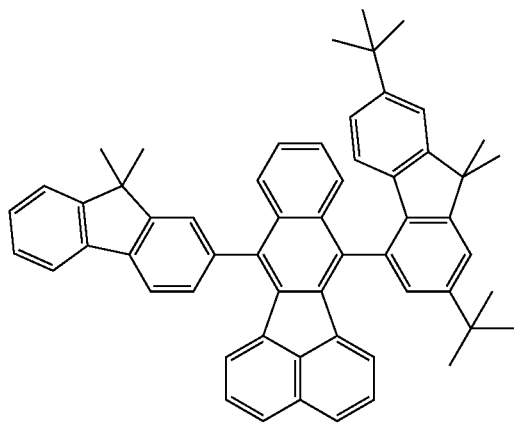
A-36
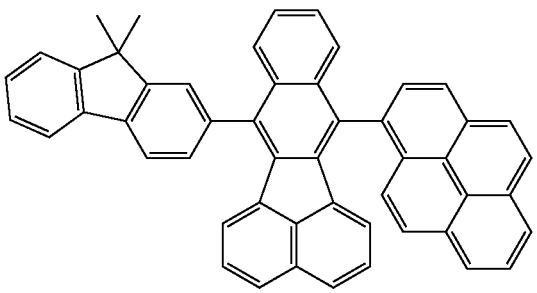
A-37
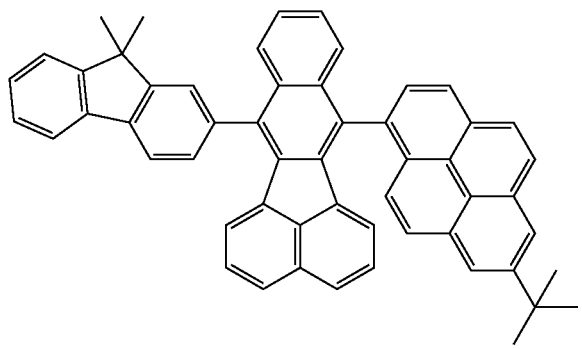
A-38
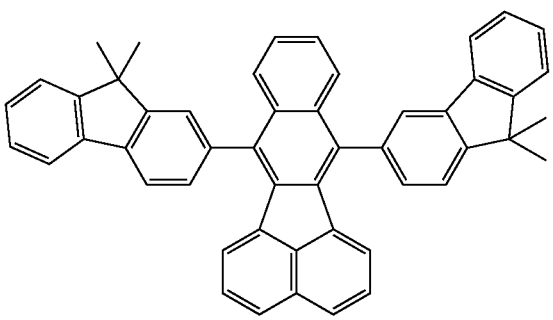
A-39
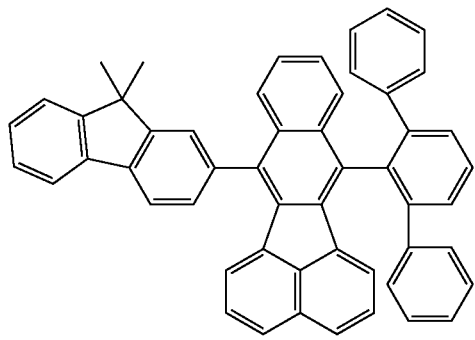
A-40
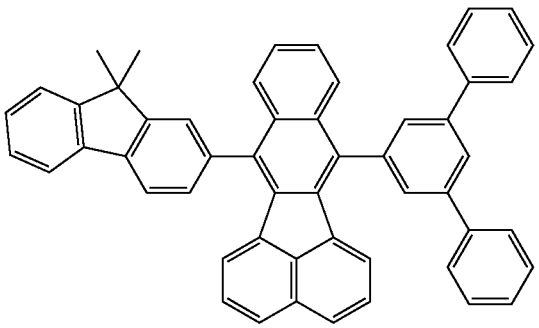
A-41
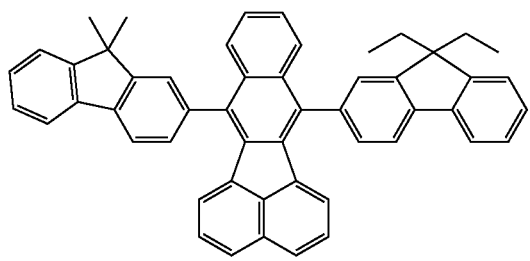
A-42
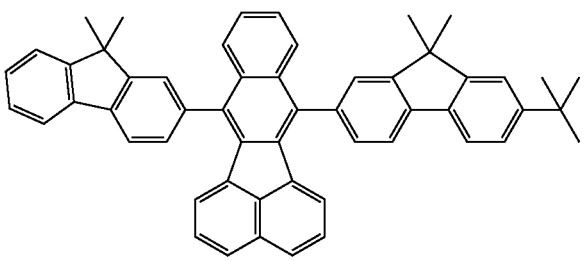

-continued
A-43
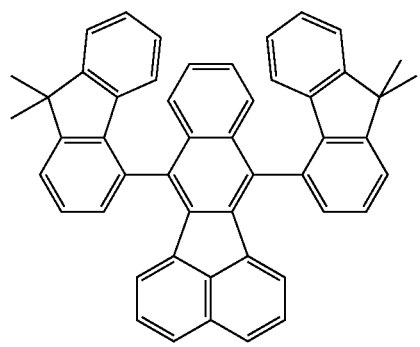
A-44
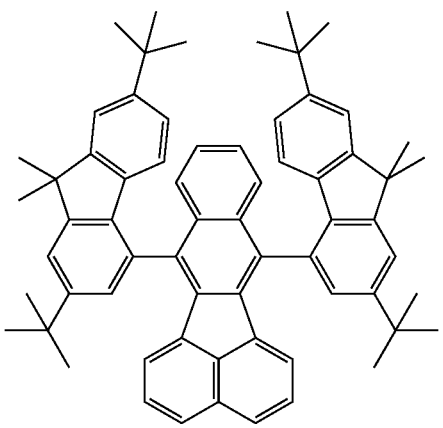
A-45
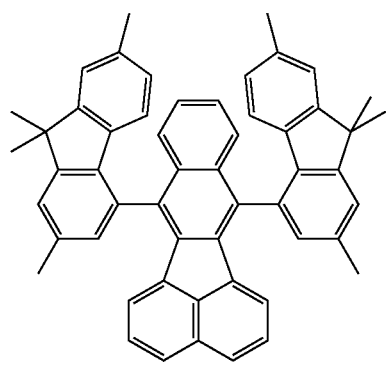
A-46
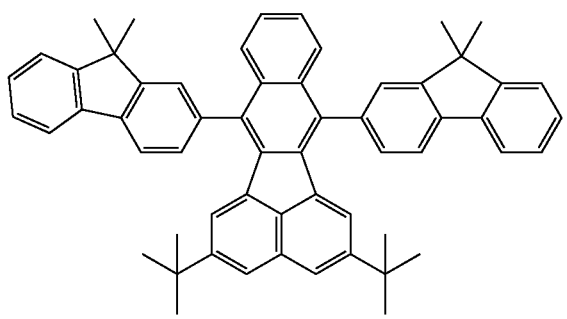
A-47
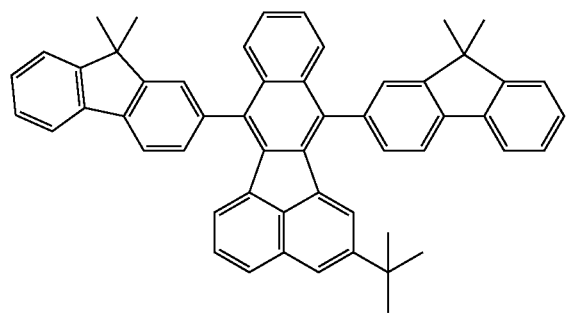
A-48
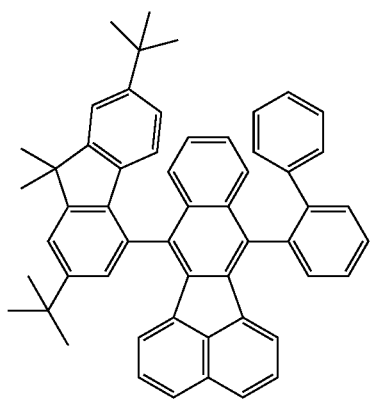
A-49
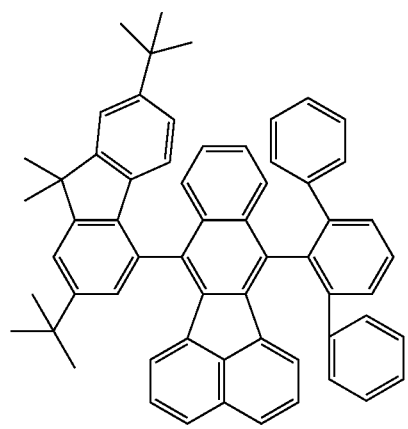
A-50
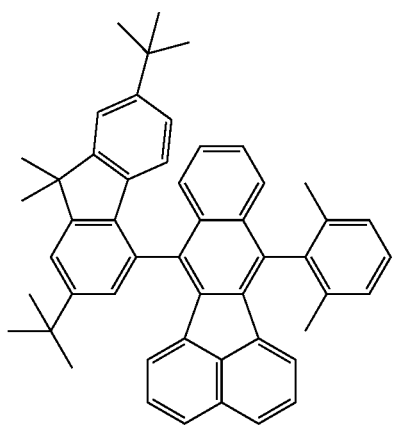

-continued
A-51
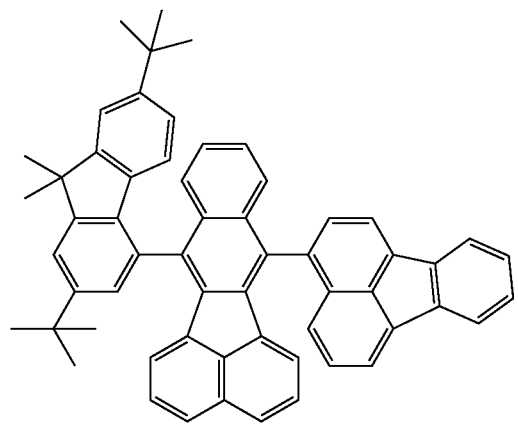
A-52
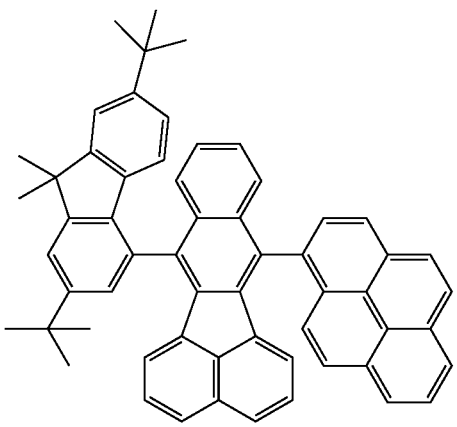
A-53
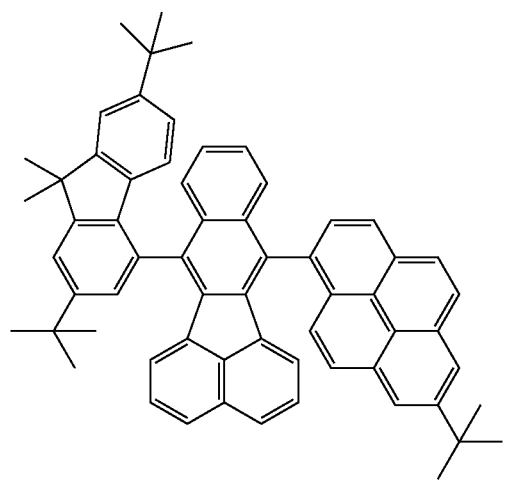
A-54
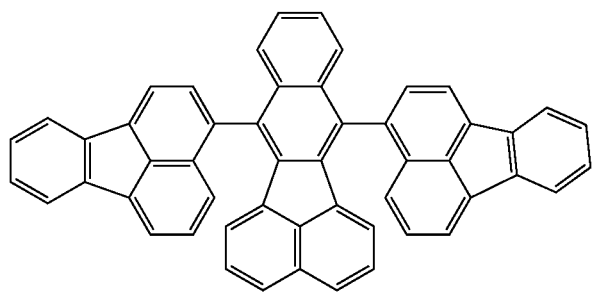
A-55
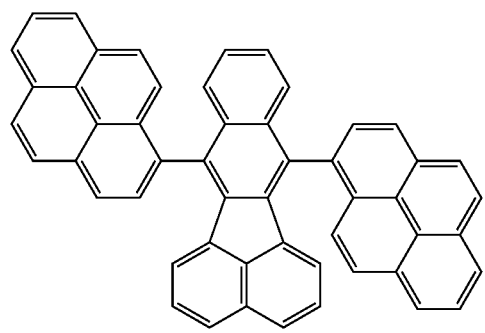
A-56
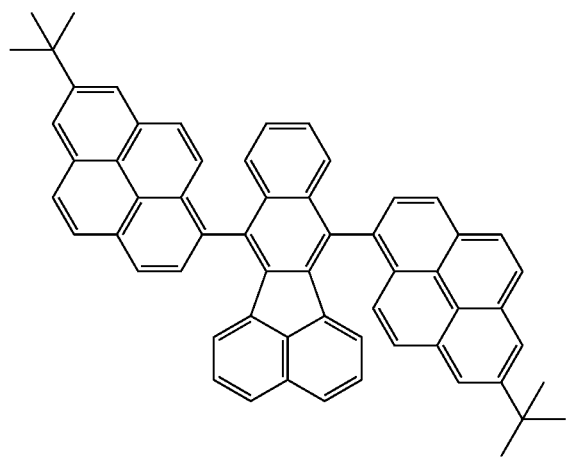

-continued
A-57
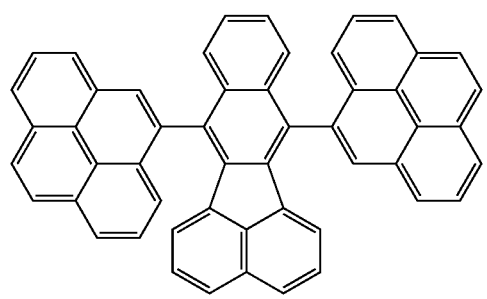
A-58
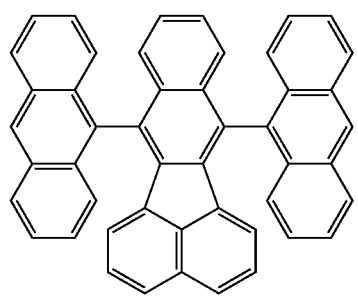
A-59
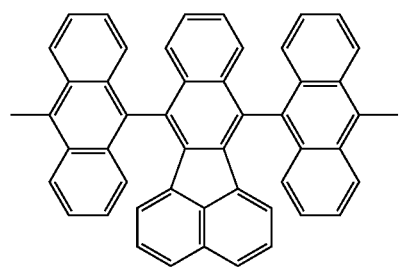
A-60
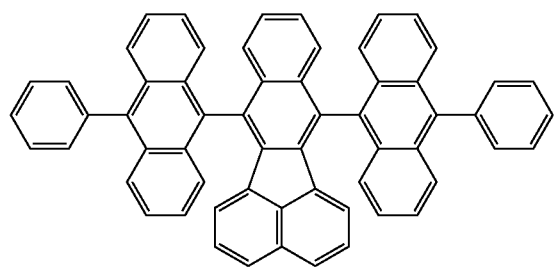
A-61
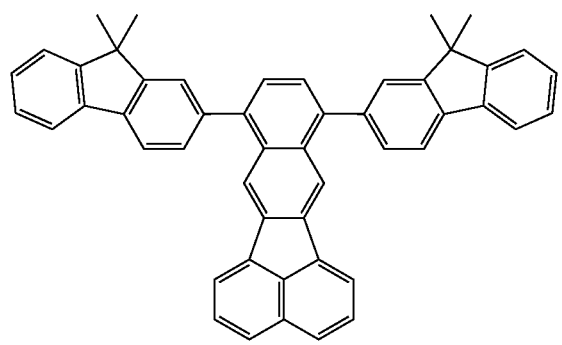
A-62
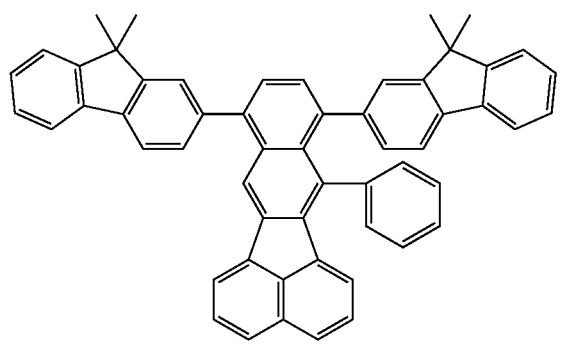
A-63
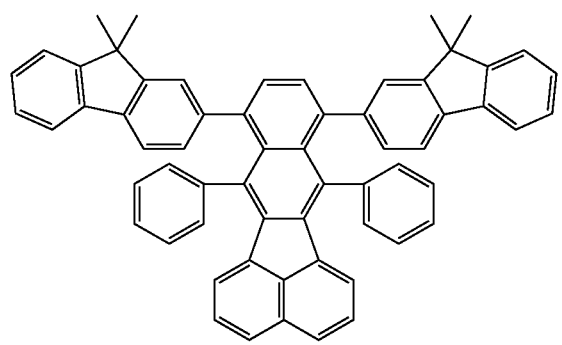
A-64
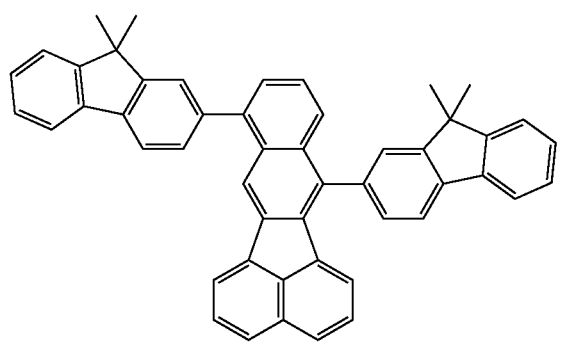

-continued

A-65
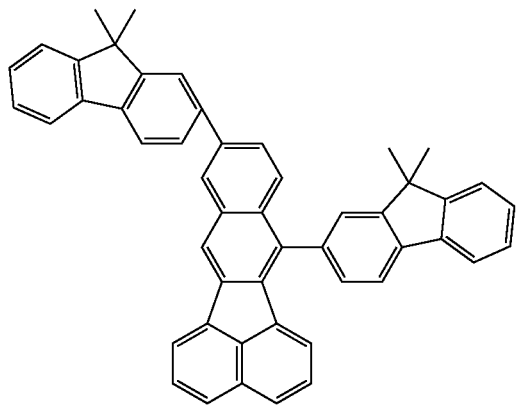

A-66
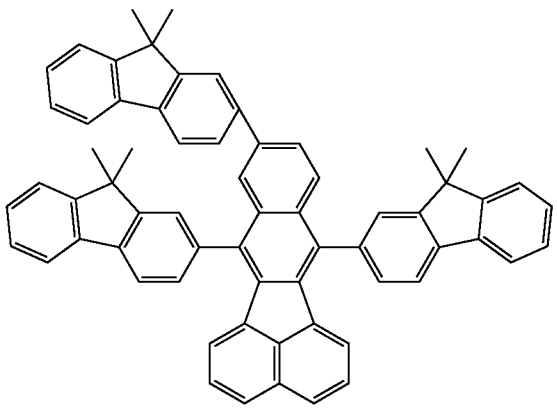

A-67
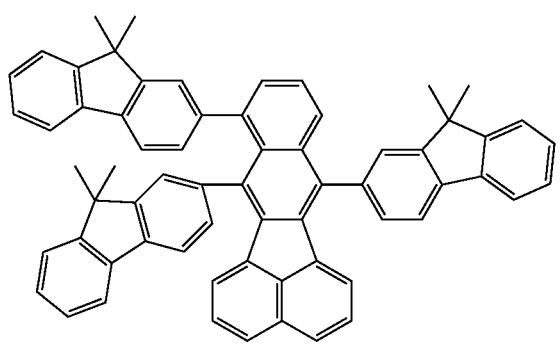

A-68
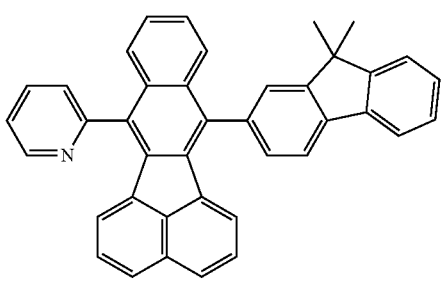

A-69
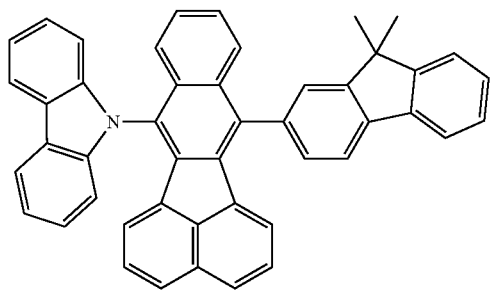

A-70
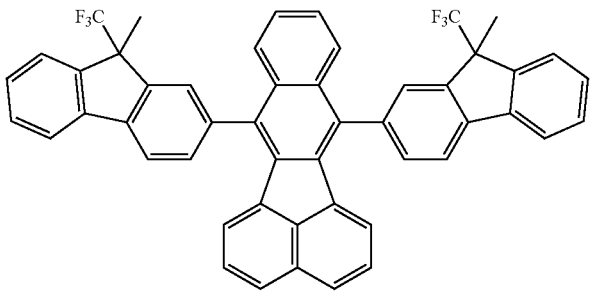

Next, an organic light emitting device of the present invention will be described in detail.

The organic light emitting device of the present invention is an organic light emitting device having at least one pair of electrodes formed of an anode and a cathode, and an organic compound layer interposed between the pair of electrodes, and the organic compound layer contains a compound represented by the general formula (I).

The organic light emitting device of the present invention may be further provided with another organic compound layer in addition to the above organic compound layer.

In the organic light emitting device of the present invention, the above organic compound layer may further contain another compound in addition to the compound represented by the general formula (I).

At least a light emitting layer among the layers each containing an organic compound of the organic light emitting device of the present invention preferably contains at least one kind of the above described compounds. In addition, in an organic light emitting device having a light emitting layer formed of two or more compounds including a host and a guest, the host or the guest is preferably the above described compound. The term "guest" as used in the present invention refers to a compound that mainly emits light in response to recombination between a hole and an electron in the light emitting region of the organic light emitting device. The guest is incorporated into another compound (host) of which the light emitting region is formed.

The content of the compound represented by the general formula (I) according to the present invention to be used as the guest is preferably 50 wt % or less, more preferably 0.1 wt % or more to 30 wt % or less, or particularly preferably 0.1 wt % or more to 15 wt % or less.

The content of the compound represented by the general formula (I) according to the present invention to be used as the host is preferably 50 wt % or less, more preferably 70 wt % or more to 99.9 wt % or less, or particularly preferably 85 wt % or more to 99.9 wt % or less.

On the other hand, when the compound represented by the general formula (I) according to the present invention is used as a host compound, the guest is not particularly limited, and, for example, a compound to be described later can be appropriately used depending on, for example, a desired luminescent color. In addition, the light emitting layer may be doped with a hole transporting compound, an electron transporting compound, or the like as required together with the guest.

The compound of the present invention, which may be used only in the light emitting layer among the organic compound layers, can be used in, for example, a hole injecting layer, a hole transporting layer, an electron injecting layer, an electron transporting layer, or an electron blocking layer in addition to the light emitting layer as required.

In the organic light emitting device of the present invention, the compound represented by the above general formula (I) is formed between the anode and the cathode by a vacuum deposition method or a solution coating method. The thickness of the organic layer may be smaller than 10 μm, preferably 0.5 μm or less, or more preferably 0.01 μm or more to 0.5 μm or less.

FIGS. 1, 2, 3, 4, 5 and 6 each show a preferable example of the organic light emitting device of the present invention.

First, provided are a substrate 1, an anode 2, a light emitting layer 3, a cathode 4, a hole transport layer 5, an electron transport layer 6, a hole injection layer 7, and a hole/exciton blocking layer 8.

FIG. 1 is a sectional view showing an example of an organic light emitting device according to the present invention. As shown in FIG. 1, the organic light emitting device has a structure in which the anode 2, the light-emitting layer 3, and the cathode 4 are provided on the substrate 1 in this order. In this example, the light emitting device including a compound having all of hole-transporting property, electron-transporting property, and light-emitting property or including compounds having the respective properties in combination, is useful.

Figure 2:
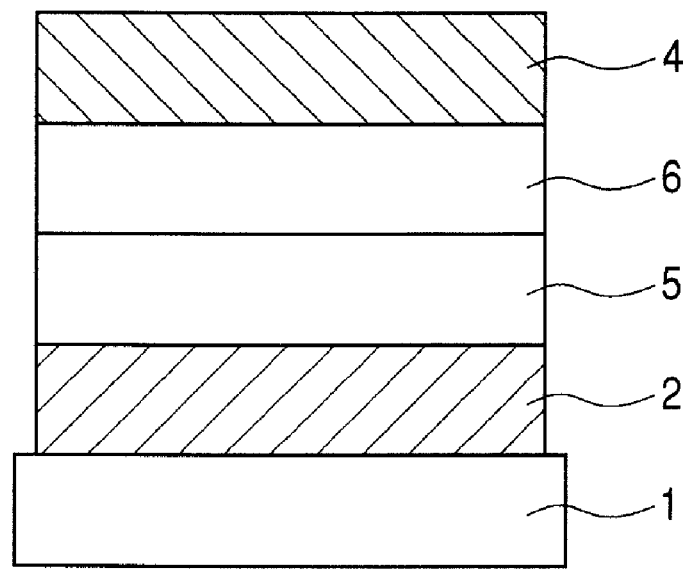
FIG. 2 is a sectional view showing another example of the organic light emitting device of the present invention.

FIG. 2 is a sectional view showing another example of the organic light emitting device according to the present invention. As shown in FIG. 2, the organic light emitting device has a structure in which the anode 2, the hole transport layer 5, the electron transport layer 6, and the cathode 4 are provided on the substrate 1 in this order. In this example, the following case is useful. That is, a light-emitting substance whose material has at least one of hole-transporting property and electron-transporting property is used for each layer, and the light-emitting substance is used in combination with a non-illuminant hole-transporting substance or electron-transporting substance. In this case, the light-emitting layer is formed of either the hole transport layer 5, or the electron transport layer 6.

Figure 3:
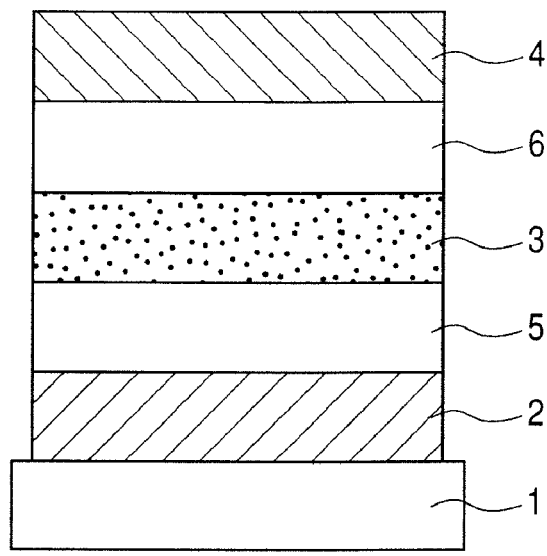
FIG. 3 is a sectional view showing still another example of the organic light emitting device of the present invention.

FIG. 3 is a sectional view showing still another example of the organic light emitting device according to the present invention. As shown in FIG. 3, the organic light emitting device has a structure in which the anode 2, the hole transport layer 5, the light emitting layer 3, the electron transport layer 6, and the cathode 4 are provided on the substrate 1 in this order. This organic light emitting device has a carrier-transporting function and a light-emitting function which are separated. This device may be used in combination with compounds each having hole-transporting property, electron-transporting property, or light-emitting property as appropriate, thereby allowing a substantial increase in freedom of choice in material to be used. Further, various compounds having different emission wavelengths can be used, thereby allowing an increase in variety of luminescent colors. Further, luminous efficiency may be improved by efficiently trapping each carrier or exciton in the light-emitting layer provided in the middle of the device.

Figure 4:
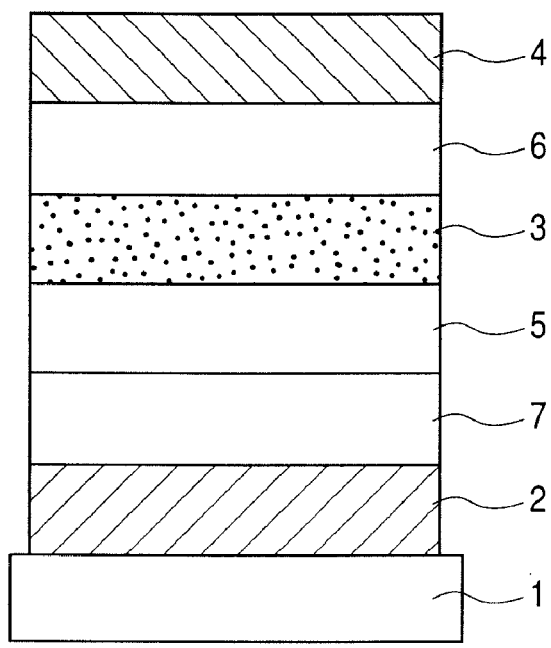
FIG. 4 is a sectional view showing yet another example of the organic light emitting device of the present invention.

FIG. 4 is a sectional view showing yet another example of the organic light emitting device according to the present invention. The organic light emitting device of FIG. 4 has a structure shown in FIG. 3 except that the hole-injecting layer 7 is inserted into a side of the anode. This structure is effective for improving adhesiveness between the anode and the hole transport layer or for improving hole-injecting property, which is effective in lowering a voltage to be applied to the device.

Figure 5:
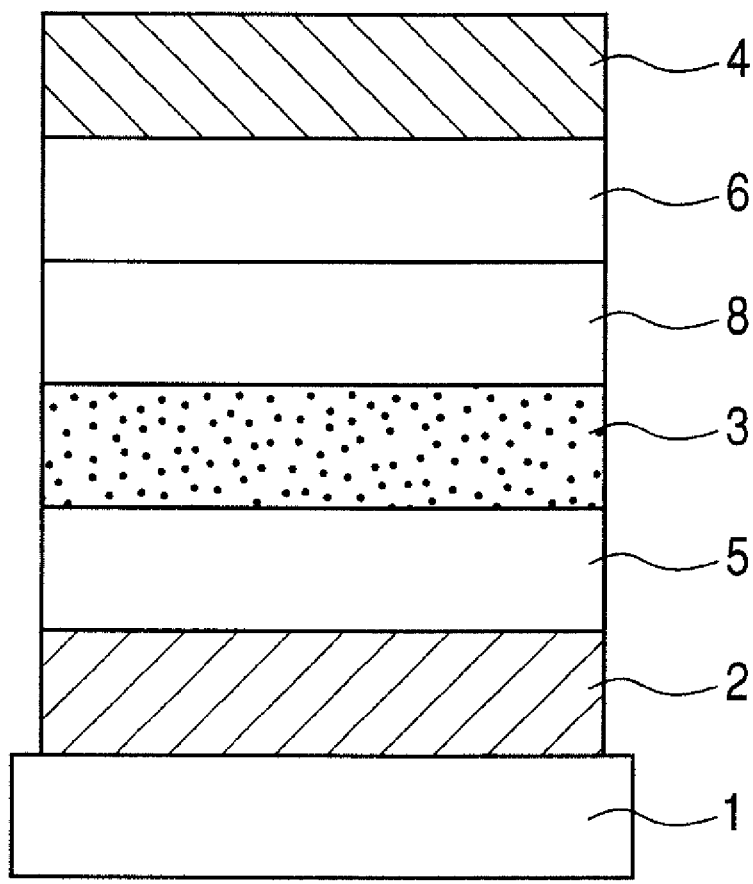
FIG. 5 is a sectional view showing still yet another example of the organic light emitting device of the present invention.
Figure 6:
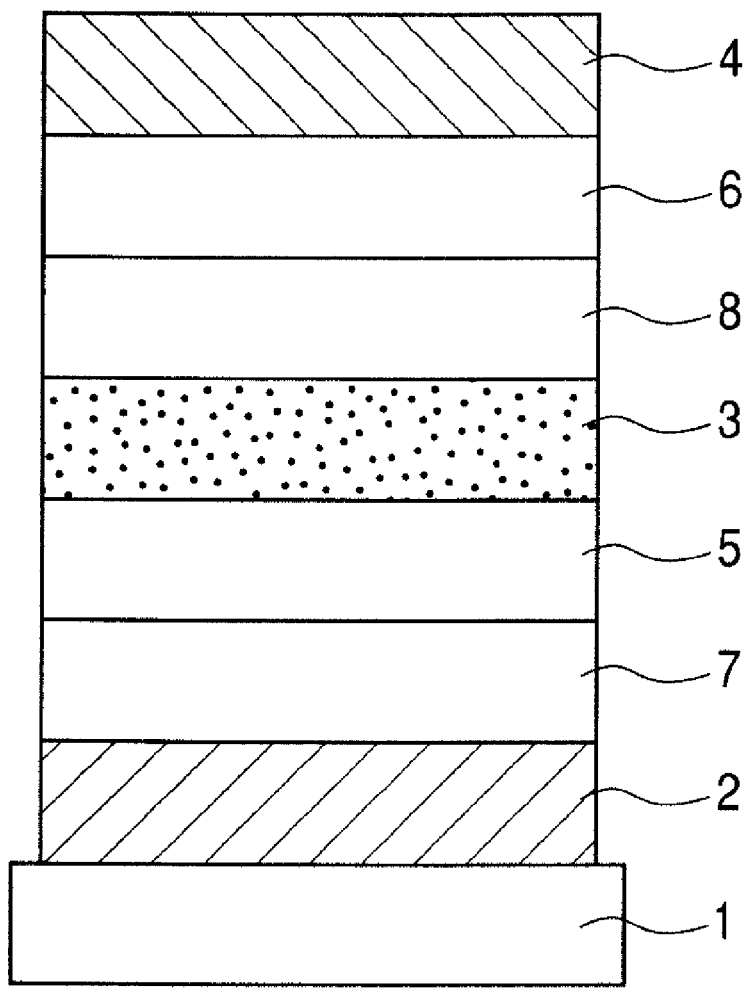
FIG. 6 is a sectional view showing still yet another example of the organic light emitting device of the present invention.

Each of FIGS. 5 and 6 is a sectional view showing still yet another example of the organic light emitting device according to the present invention. The organic light emitting device of FIG. 5 has a structure shown in FIG. 3 except that a layer (the hole/exciton-blocking layer 8) for blocking travel of a hole or exciton to a side of the cathode is inserted between the light-emitting layer and the electron transport layer. The organic light emitting device of FIG. 6 has a structure shown in FIG. 4 except that a layer (the hole/exciton-blocking layer 8) for blocking travel of a hole or exciton to a side of the cathode is inserted between the light-emitting layer and the electron transport layer. Each of those structures uses a compound having an extremely high ionization potential in the hole/exciton-blocking layer 8 and is effective for improving luminous efficiency.

However, FIGS. 1, 2, 3, 4, 5 and 6 each show a basic device structure, and the structure of the organic light emitting device using the compound of the present invention is not limited to the structures described above. For example, the organic light emitting device of the present invention may have any one of various layer structures including: a structure having an insulating layer provided at an interface between the electrode and the organic layer; a structure having an adhesive layer or an interference layer provided; and a structure in which a hole transport layer is composed of two layers with different ionization potentials.

The compound shown in the formula (I) of the present invention may be used for any of the structures shown in FIGS. 1, 2, 3, 4, 5 and 6.

In the present invention, the compound represented by the general formula (I) is used as a constituent component for the light emitting layer; a conventionally known hole transporting compound, luminous compound, electron transporting compound, or the like can be used together with the compound as required.

Hereinafter, examples of those compounds are shown.

33
Hole Transporting Compounds
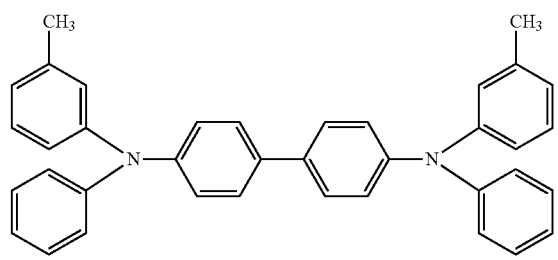
TPD
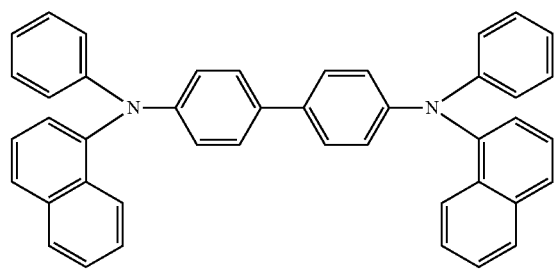
a-NPD
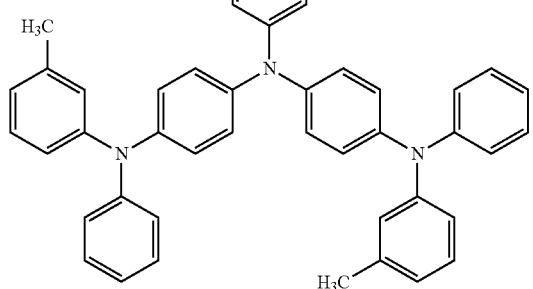
m-MTDATA
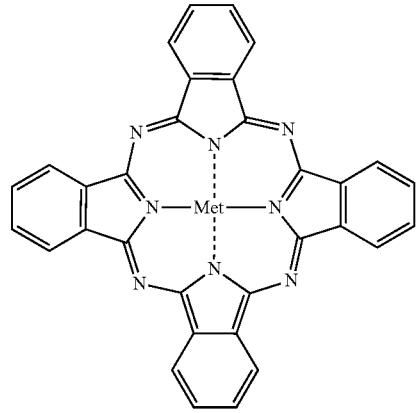
Met = Cu, Mg, AlCl, TiO$_2$, SnCl$_2$, etc.
Met-Pc
34
Hole Transporting Compounds
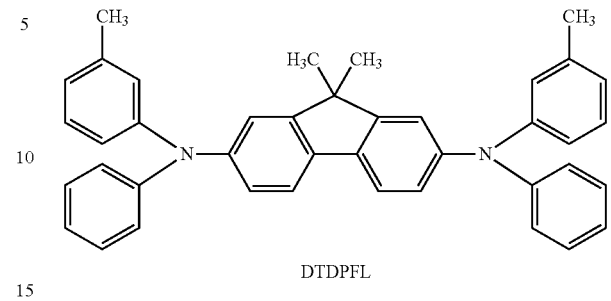
DTDPFL
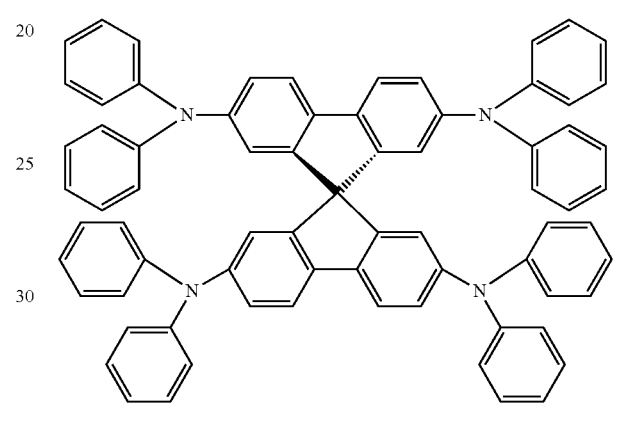
spiro-TPD
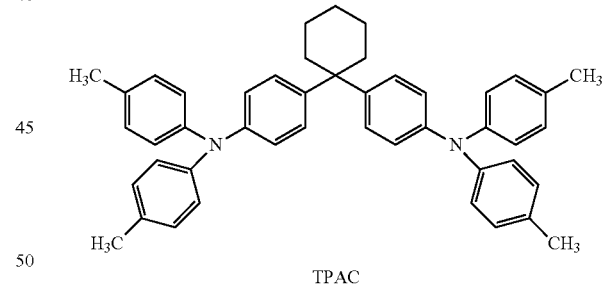
TPAC
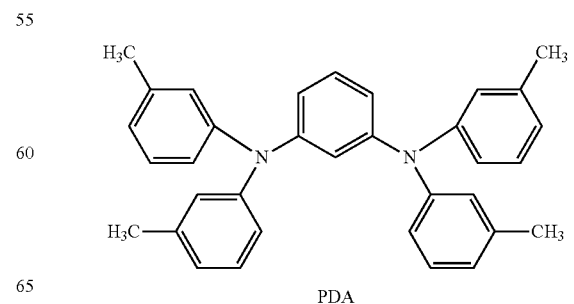
PDA Electron-Transporting Light-Emitting Materials
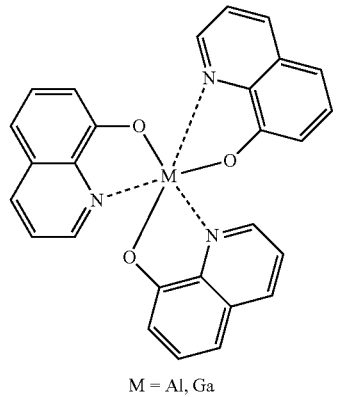
M = Al, Ga
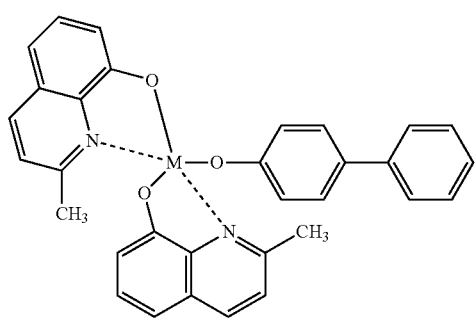
M = Al, Ga
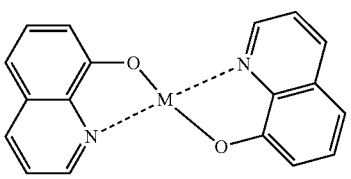
M = Zn, Mg, Be
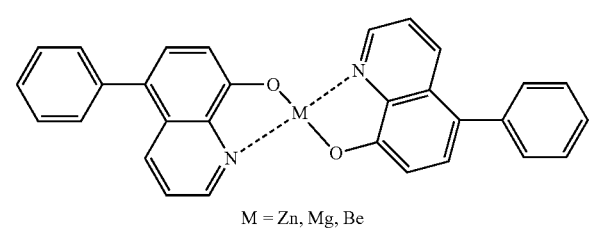
M = Zn, Mg, Be
Electron-Transporting Light-Emitting Materials
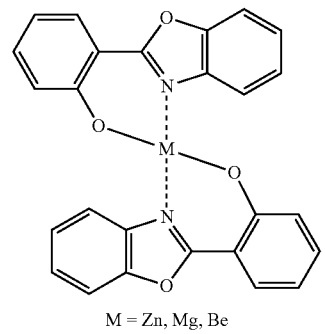
M = Zn, Mg, Be
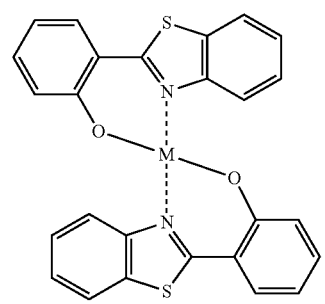
M = Zn, Mg, Be
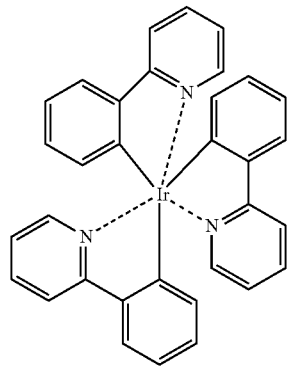
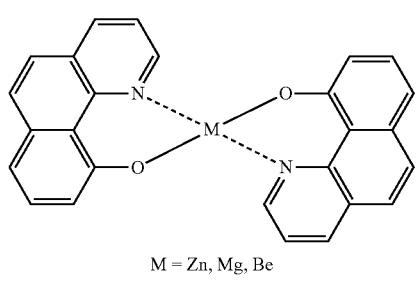
M = Zn, Mg, Be

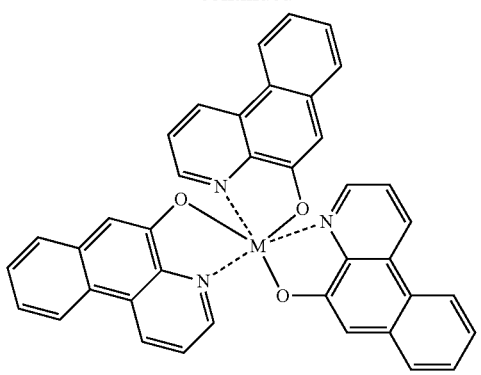
M = Al, Ga
Light Emitting Materials
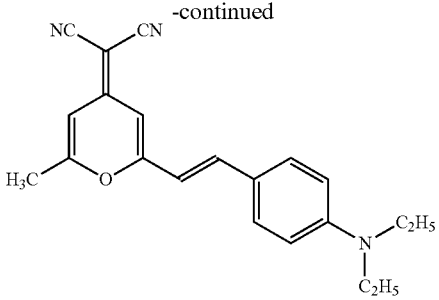
DCM-1
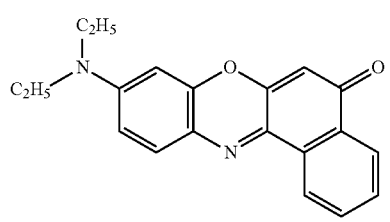
Nile red
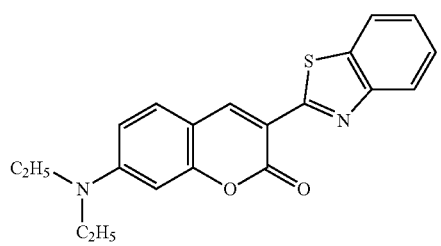
Coumarin 6
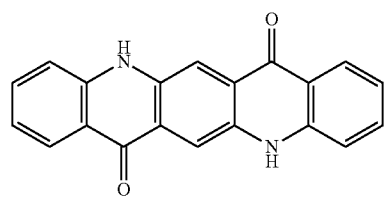
Quinacridone
Light Emitting Materials
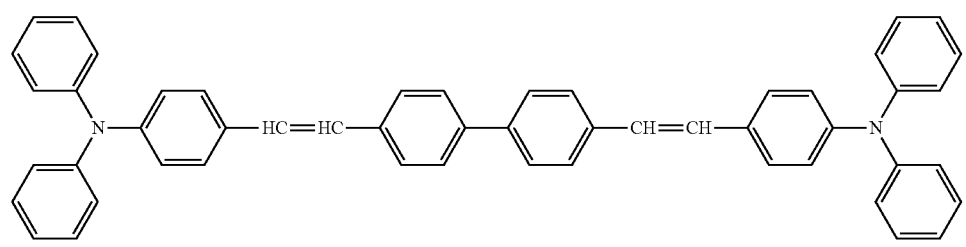
DPABVi
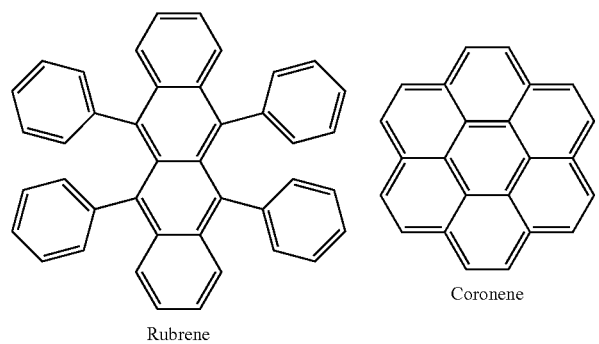
Rubrene          Coronene Light-Emitting Layer Matrix Materials and Electron-Transporting Materials
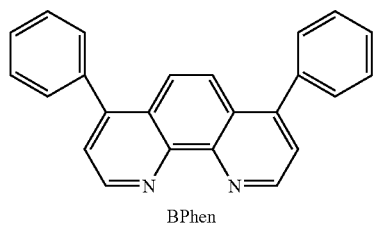
BPhen
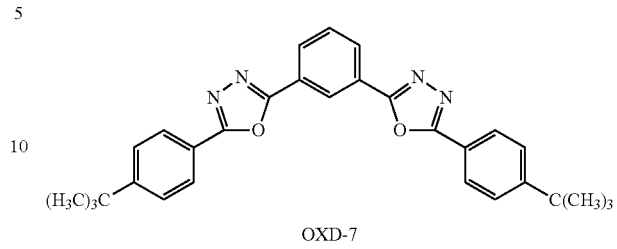
OXD-7
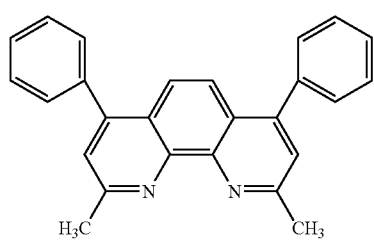
BCP
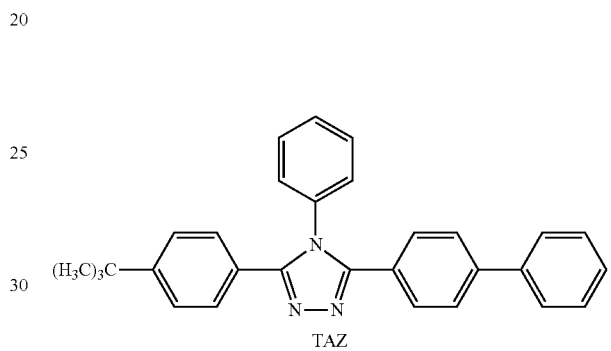
TAZ
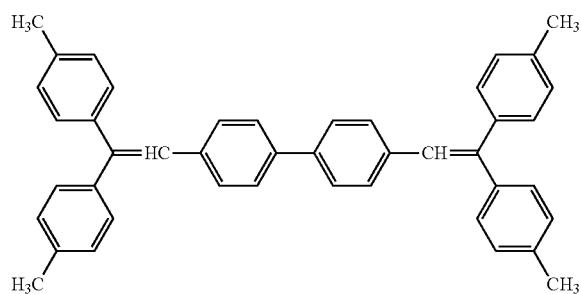
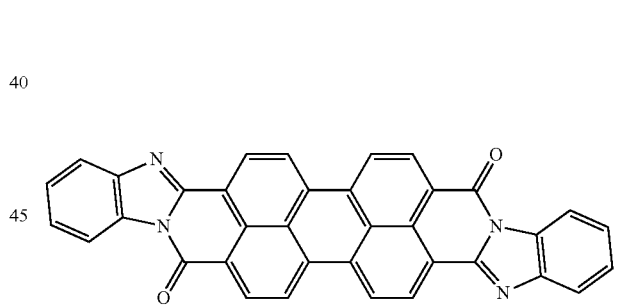
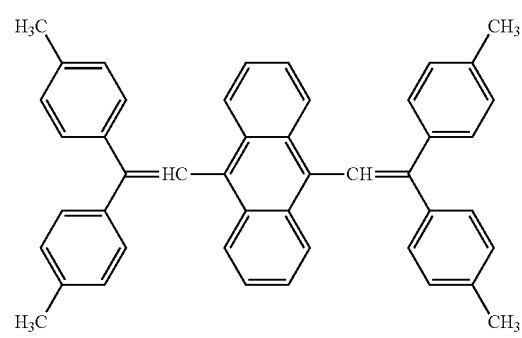
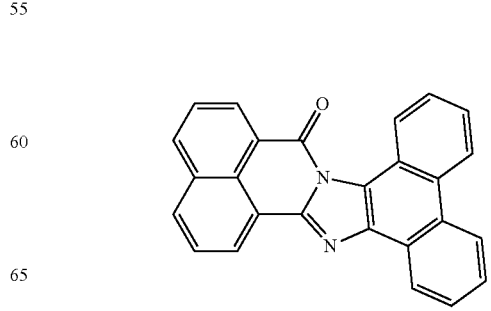

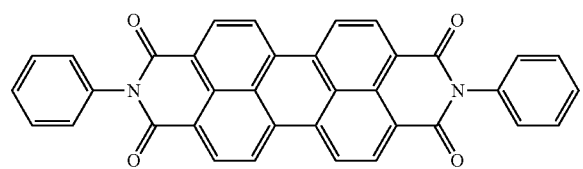
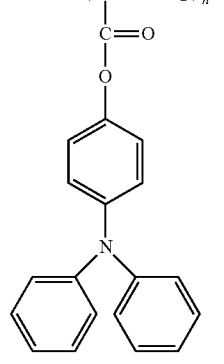
TPA-PMMA
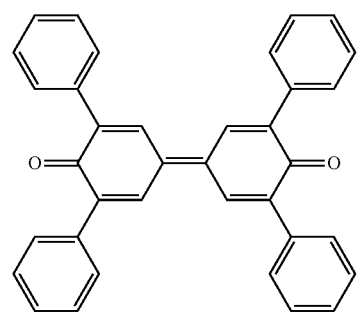
Polymeric Hole Transporting Materials
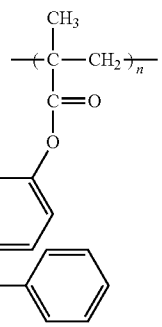
TPD-PMMA
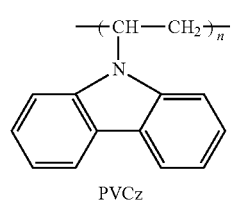
PVCz
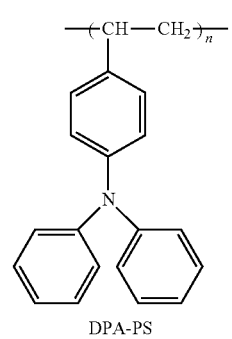
DPA-PS
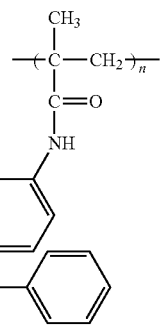
TPD-PMAA Polymeric Hole Transporting Materials

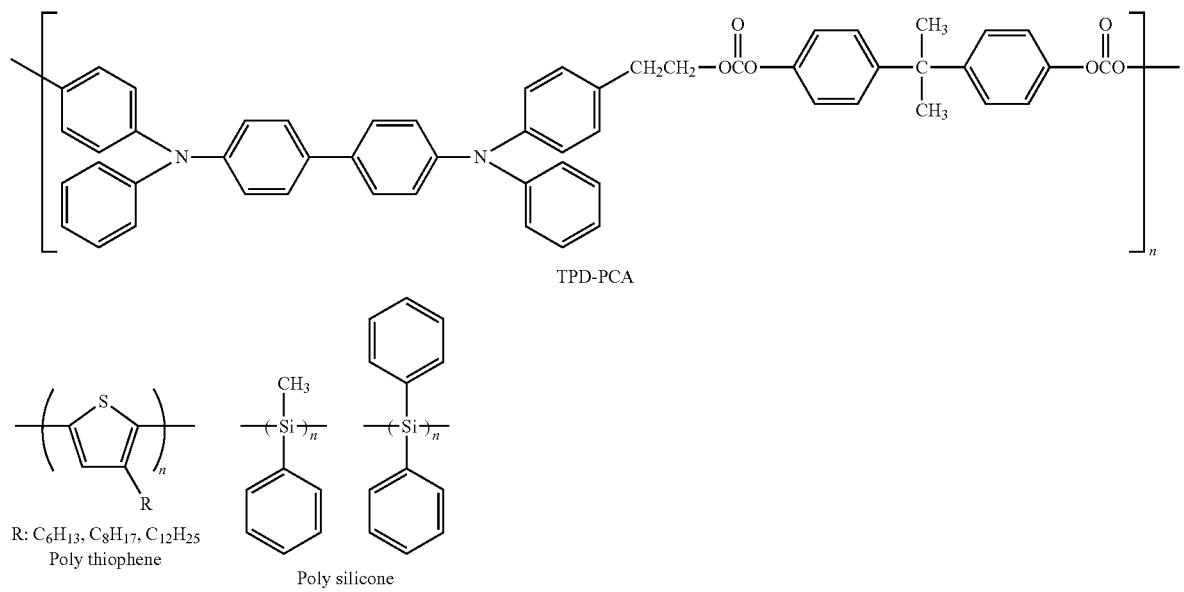
TPD-PCA

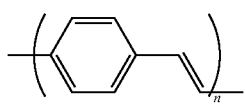

R: $C_6H_{13}$, $C_8H_{17}$, $C_{12}H_{25}$
Poly thiophene

Poly silicone

Polymeric Light Emitting Materials and Charge Transporting Materials

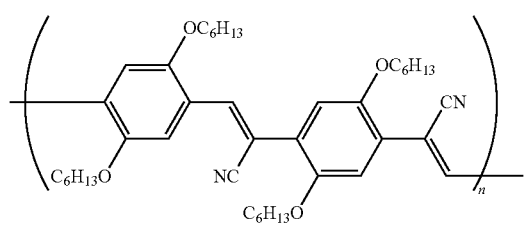

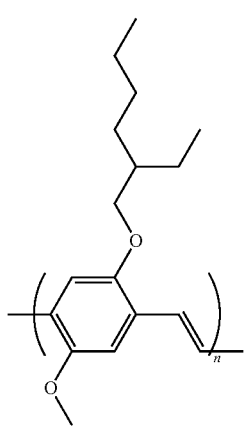

-continued

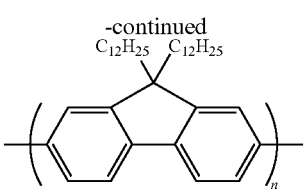

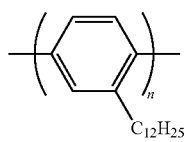

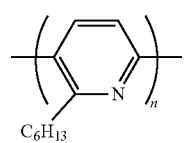

In the organic light emitting device according to the present invention, the layer containing the compound shown in the formula (I) and layers containing other organic compounds may be formed generally by a vacuum deposition method or by a coating method in which the compound is dissolved in an appropriate solvent. In film formation by the coating method, in particular, a film may be formed by using the compound in combination with an appropriate binder resin.

The binder resin may be selected from a wide variety of binder resins. Examples of the binder resin include, but not limited to: a polyvinyl carbazole resin; a polycarbonate resin; a polyester resin; a polyarylate resin; a polystyrene resin; an acrylic resin; a methacrylic resin; a butyral resin; a polyvinyl acetal resin; a diallyl phthalate resin; a phenol resin; an epoxy resin; a silicone resin; a polysulfone resin; and a urea resin. These resins may be used alone, or in combination of at least two kinds thereof as a homopolymer or copolymer.

An anode material may have as large a work function as possible, and examples thereof include: a metal simple substance such as gold, platinum, nickel, palladium, cobalt, selenium, or vanadium; an alloy thereof; and a metal oxide such as tin oxide, zinc oxide, indium tin oxide (ITO), or indium zinc oxide. Further, a conductive polymer such as polyaniline, polypyrrole, polythiophene, or polyphenylene sulfide may also be used. Each of those electrode materials may be used alone, or two or more kinds thereof may be used in combination.

Meanwhile, a cathode material may have a small work function, and examples thereof include: a metal simple substance such as lithium, sodium, potassium, cesium, calcium, magnesium, aluminum, indium, silver, lead, tin, or chromium; and an alloy of two or more kinds thereof. A metal oxide such as indium tin oxide (ITO) may also be used. Further, the cathode may have a single layer structure or a multilayer structure.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate. In addition, the substrate may have a color filter film, a fluorescent color converting filter film, a dielectric reflection film, or the like for controlling luminescent color.

Further, a protective layer or a sealing layer may be formed on the fabricated device to prevent contact between the device and oxygen, moisture, or the like. Examples of the protective layer include: a diamond thin film; a film formed of an inorganic material such as metal oxide or metal nitride; a polymer film formed of a fluorine resin, polyparaxylene, polyethylene, a silicone resin, a polystyrene resin, or the like; and a photocurable resin. Further, the device itself may be covered with glass, a gas-impermeable film, a metal, or the like and packaged with an appropriate sealing resin.

In addition, the present invention is characterized in that the light emitting region contains a compound having a benzo[k]fluoranthene skeleton as a guest material and a compound having a condensed ring hydrocarbon skeleton which is tetracyclic or more as a host material. Examples of the condensed ring hydrocarbon skeleton which is tetracyclic or more include a pyrene skeleton, a fluoranthene skeleton, a benzofluoranthene skeleton, a tetracene skeleton, a triphenylene skeleton, and a chrysene skeleton. Of those, the pyrene skeleton or the fluoranthene skeleton is preferable from the viewpoints of a band gap and carrier transporting property.

Examples of a compound having a pyrene skeleton include, but not limited to, the following materials.

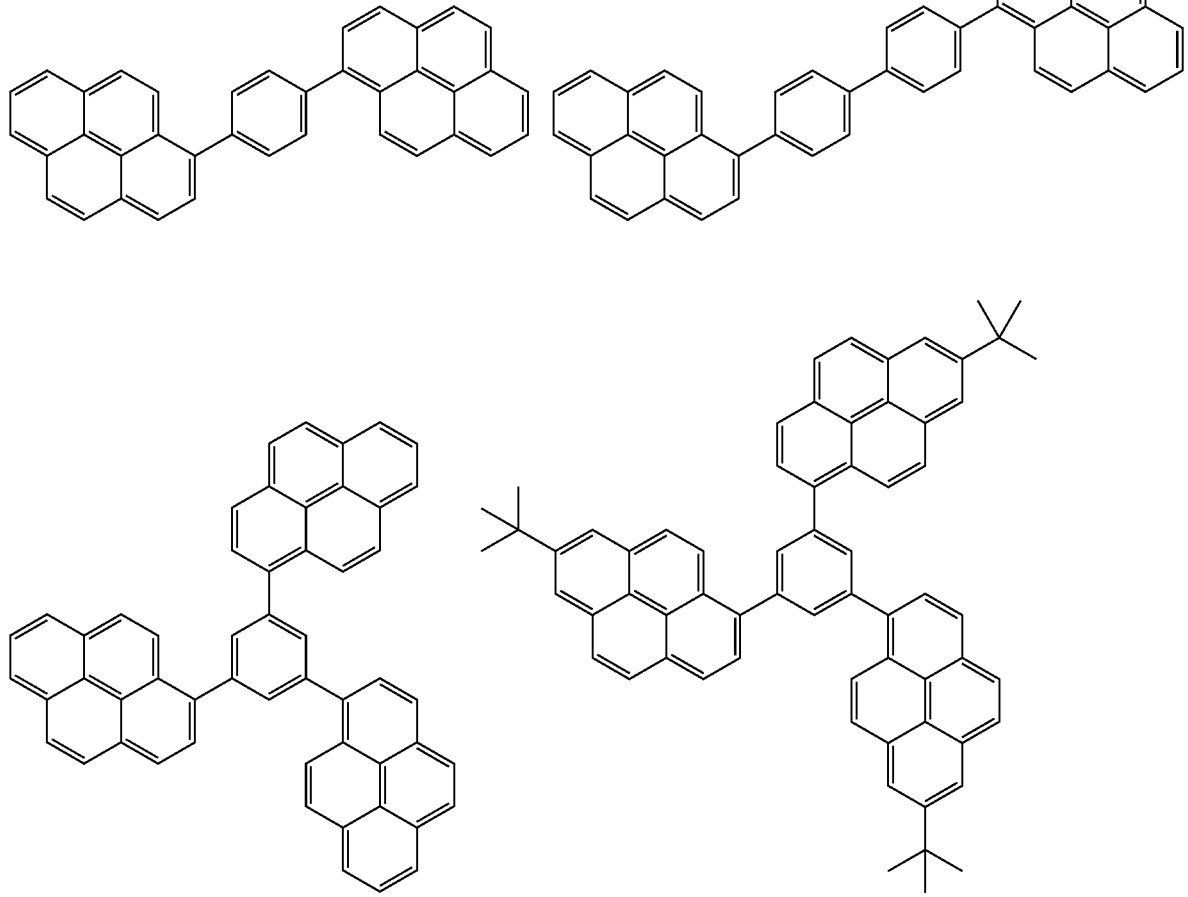

-continued
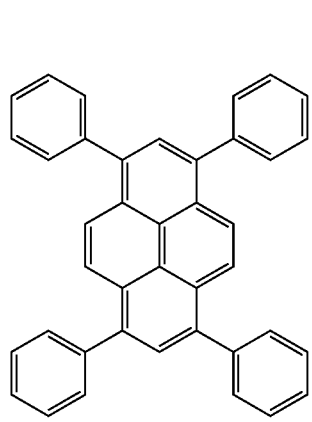 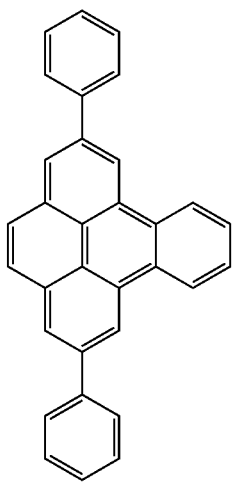 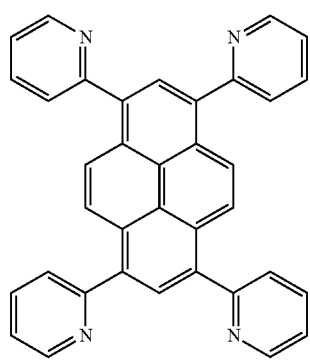
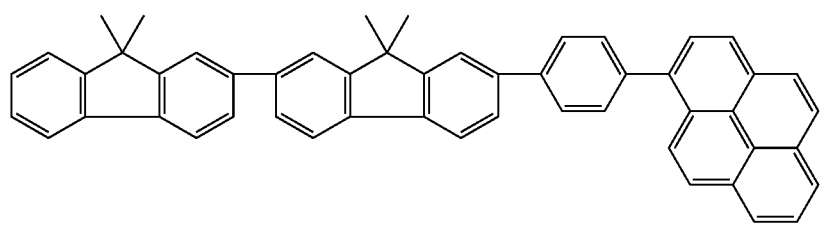
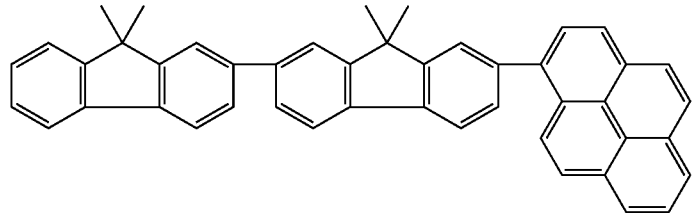
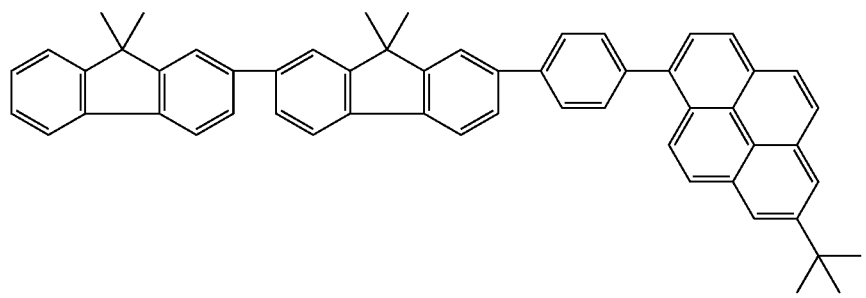
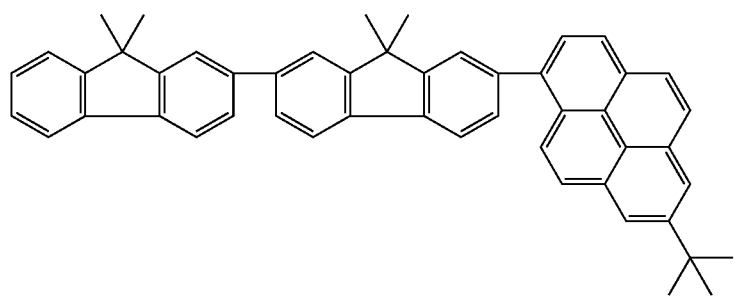

In addition, the compound having a benzo[k]fluoranthene skeleton as the guest used in the present invention is not particularly limited; a compound represented by any of the above general formulae (I) to (V) of the present invention is preferably used as the compound.

Further, the host and the guest preferably have the same condensed ring aromatic structure. The introduction of the same condensed ring aromatic structure into the molecular structures of the materials, that is, the host and the guest improves compatibility between the host and the guest, whereby a light emitting device having good durability may be achieved. Examples of the above condensed ring aromatic structure include a naphthalene skeleton, a fluorene skeleton, a pyrene skeleton, a fluoranthene skeleton, a benzofluoranthene skeleton, a tetracene skeleton, a triphenylene skeleton, and a chrysene skeleton. Of those, the fluoranthene skeleton is particularly preferable from the viewpoints of a band gap and an oscillator strength.

EXAMPLES

Hereinafter, the present invention will be described more specifically by way of examples. However, the present invention is not limited to these examples.

It should be noted that a benzo[k]fluoranthene derivative represented by a general formula (I) can be produced in accordance with the following production method by, for example, a Diels-Alder reaction between Compound 1 and Compound 2 or a Diels-Alder reaction between Compound 3 and Compound 4.

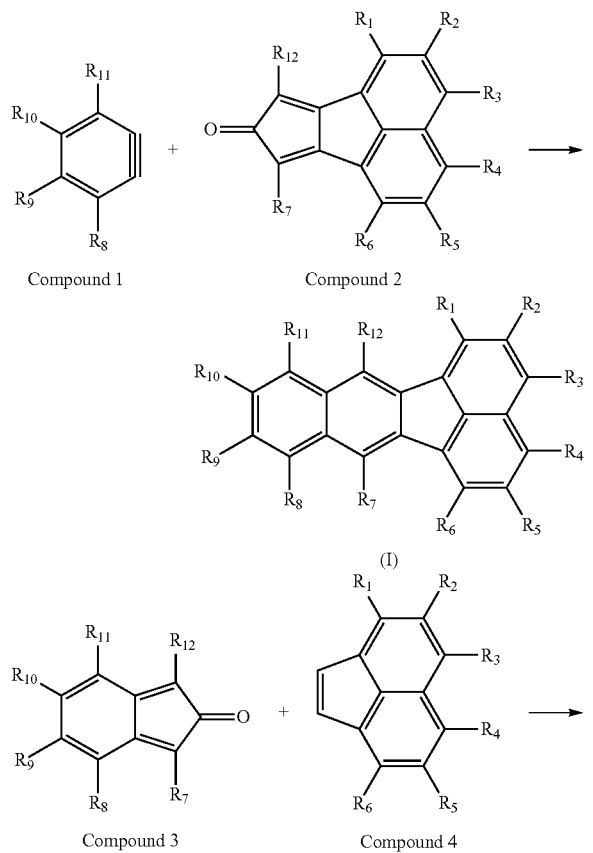

Example 1

Synthesis of Exemplified Compound No. A-1

(1-1) Synthesis of Synthetic Intermediate Compound 6

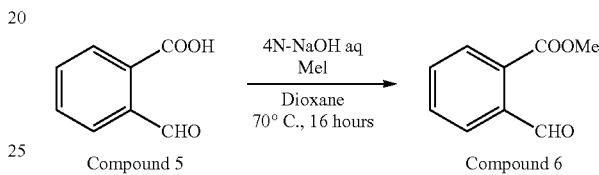

41 g (0.273 mol) of 2-carboxybenzaldehyde (Compound 5), 410 mL of dioxane, 80 mL of iodomethane, and 82 mL (0.328 mol) of a 4N aqueous solution of sodium hydroxide were added to a 1-L reaction vessel. The solution was vigorously stirred at 70° C. for 16 hours. Dioxane was removed under reduced pressure, and 200 mL of distilled water was added to the solution, followed by extraction with ethyl acetate (200 mL×twice). An organic layer was collected, washed with saturated sodium bicarbonate water, distilled water, and a saturated salt solution, and dried with anhydrous MgSO$_4$. After that, the solution was condensed, whereby 43 g of a colorless liquid was obtained. The liquid was purified by means of silica gel column chromatography (mobile phase; hexane:ethyl acetate=3:1), whereby 37.7 g (0.230 mol, yield=84%) of Compound 6 as a colorless liquid were obtained.

(1-2) Synthesis of Synthetic Intermediate Compound 7

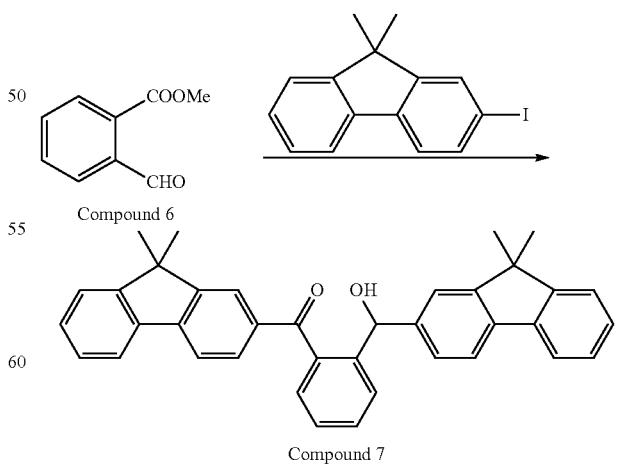

58.5 g (183 mmol) of 2-iodo-9,9-dimethylfluorene and 600 mL of diethyl ether were added to a 1-L reaction vessel. The solution was cooled to −78° C., and 116 mL (183 mmol) of a solution of n-butyllithium in hexane having a concentration of 1.57 mol/L was added to the solution over 10 minutes. After the solution had been stirred at the temperature for 30 minutes, Compound 6 (15 g, 91.3 mmol) dissolved in 100 mL of diethyl ether and cooled to −20° C. was added to the solution in one stroke. The solution was heated to room temperature while a cooling bath was attached, and 300 mL of 10% ammonia water was added to the suspension, followed by extraction with ethyl acetate (200 mL×twice). An organic layer was collected, washed with distilled water and a saturated salt solution, and dried with anhydrous MgSO₄. After that, the solution was condensed and dried in a high vacuum, whereby 53.6 g of Compound 7 as a tan solid was obtained.

(1-3) Synthesis of Exemplified Compound No. A-1 diethyl ether was added to the suspension to precipitate a crystal. The crystal was taken by filtration and purified by means of silica gel column chromatography (mobile phase; chloroform:hexane=1:3 to chloroform:hexane=1:2) again, whereby a reddish brown solid was obtained. The solid was suspended in a small amount of chloroform, and diethyl ether was added to the suspension, followed by filtration. After that, the resultant crystal was dried in a vacuum, and was then subjected to sublimation purification, whereby 23.6 g (36.3 mmol, 40% yield) of Exemplified Compound No. A-1 was obtained.

Matrix-assisted laser desorption/ionization time-of-flight mass spectrometry (MALDI-TOF MS) confirmed that the compound had an M+ of 636.3.

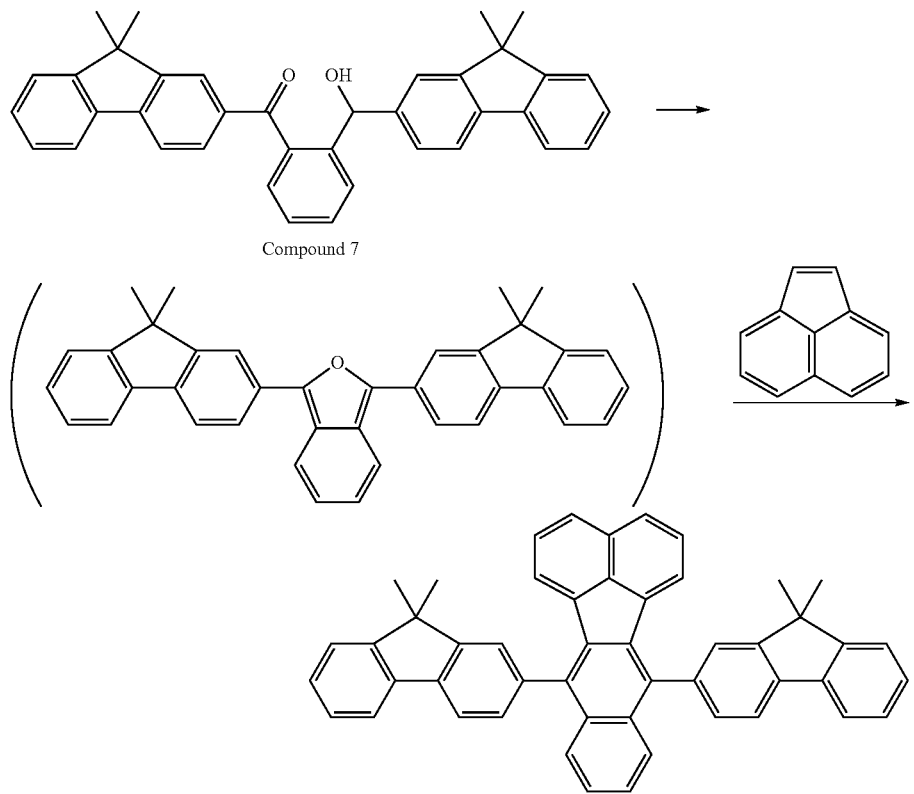

Compound 7 as a solid was loaded into a 1-L reaction vessel, and 600 mL of xylene, 5.2 g (27.3 mol) of p-toluenesulfonic acid, and 13.9 g (91.3 mmol) of acenaphthylene were added to the vessel. The solution was vigorously stirred at 150° C. for 36 hours. Xylene was removed under reduced pressure, and 100 mL of saturated sodium bicarbonate water and 400 mL of distilled water were added to the solution, followed by extraction with chloroform (500 mL×twice). An organic layer was collected, washed with saturated sodium bicarbonate water, distilled water, and a saturated salt solution, and dried with anhydrous MgSO₄. After that, the desiccant was separated by filtration. 600 g of silica gel was added to the filtrate, and the solvent was condensed and removed, whereby a black silica gel carrier was obtained. The carrier was purified by means of silica gel column chromatography (mobile phase; chloroform:hexane=1:3 to chloroform:hexane=1:1), whereby a reddish brown solid was obtained. The solid was suspended in a small amount of chloroform, and The glass transition temperature of the compound in a glass state was measured with a DSC (Pyris 1) manufactured by PerkinElmer from room temperature at a rate of temperature increase of 20° C./min. As a result, the glass transition temperature was 196° C. In addition, the compound was heated to its melting point. However, no recrystallization was observed, so it was confirmed that the compound was a material having high glass property.

In addition, the structure of the compound was identified by NMR measurement.

¹H NMR(CDCl₃, 400 MHz) σ (ppm): 8.04 (d, 2H, J=7.6 Hz), 7.90 (d, 2H, J=6.7 Hz), 7.79 (m, 2H), 7.67 (m, 4H), 7.55 (m, 4H), 7.47-7.39 (m, 6H), 7.24 (m, 2H), 6.71 (m, 2H), 1.59 (s, 6H), 1.57 (s, 6H).

In addition, a dilute solution of the compound in toluene having a concentration of 1×10⁻⁵ mol/l was prepared, and the emission spectrum of the solution was measured with a fluorescence spectrophotometer F-4500 manufactured by Hitachi, Ltd. In addition, the absorption spectrum of the solution was measured with an ultraviolet and visible spectrophotometer V-560. Further, a solution of the compound in chloroform with its concentration adjusted to 0.1 wt % was applied onto a glass substrate by spin coating, and the absorption spectrum and emission spectrum of the solution were measured. Then, the quantum yield of the compound in a thin film was measured. The luminous wavelength of benzo[k]fluoranthene as a comparative substance was also measured.

TABLE 1

| In a solution having a concentration of $1.0 \times 10^{-5}$ mol/l | |
|---|---|
| | Luminous wavelength |
| Compound No. A-1 | 431 nm |
| Benzo[k]fluoranthene | 410 nm |

TABLE 2

| Thin film | |
|---|---|
| | Luminous wavelength |
| Compound No. A-1 | 449 nm |
| Benzo[k]fluoranthene | No light emission |

In addition, the highest occupied molecular orbital (HOMO) energy of the compound was measured by photoelectron spectroscopy (measuring device name AC-1 manufactured by RIKENKIKI CO., LTD). The lowest unoccupied molecular orbital (LUMO) energy of the compound was calculated from a measured value for an energy gap and the above HOMO energy. The HOMO energy was −5.89 eV, and the LUMO energy was −2.98 eV.

Comparative Example 1

Synthesis of Comparative Compound 13

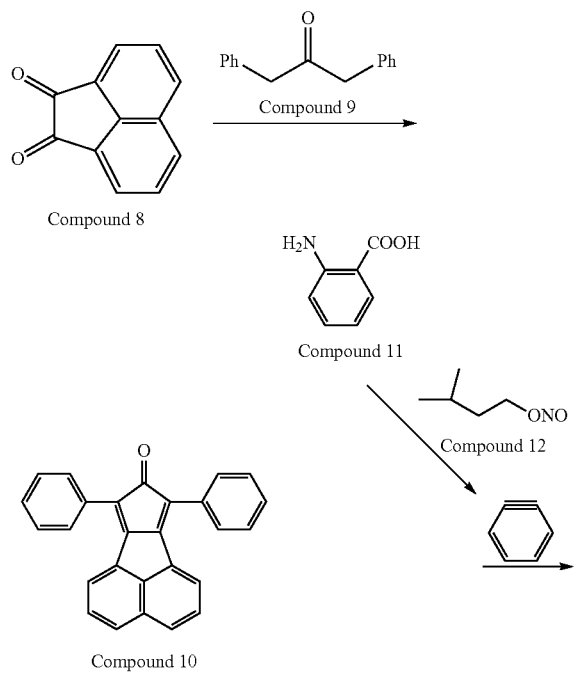

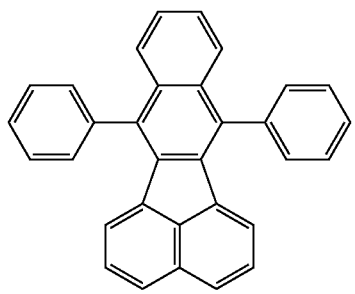

Comparative Compound 13

1.82 g (10.0 mmol) of Compound 8, 2.62 g (12.5 mmol) of Compound 9, and 50 ml of ethanol were loaded into a 100-ml three-necked flask. In a nitrogen atmosphere, the mixture was heated to 75° C., and was stirred for 2 hours. The resultant solution was cooled, and was then filtrated. The resultant black solid was washed with 10 ml of methanol, whereby 1.91 g (53.8% yield) of Compound 10 as a blackish green solid were obtained.

1.0 g (2.91 mmol) of Compound 10, 0.55 g (4.00 mmol) of Compound 11, 3.0 ml of isoamyl nitrite Compound 12, and 50 ml of tetrahydrofuran were loaded into a 100-ml three-necked flask. In a nitrogen atmosphere, the mixture was heated to 55° C., and was stirred for 4 hours. After the reaction, the resultant solution was condensed and purified with a silica gel column (heptane+toluene mixed developing solvent), whereby 0.840 g (71.5% yield) of Comparative Compound 13 (whitish yellow crystal) was obtained.

In addition, the structure of the compound was identified by NMR measurement.

$^1$H NMR(CDCl$_3$, 400 MHz) σ (ppm): 7.63-7.70 (m, 10H), 7.57 (d, 4H), 7.40 (m, 2H), 7.32 (t, 2H), 7.61 (d, 2H).

The glass transition temperature of the compound in a glass state was measured with a DSC (Pyris 1) manufactured by PerkinElmer from room temperature at a rate of temperature increase of 20° C./min, and the glass transition temperature was 96° C.

In addition, the luminous wavelength of the compound was measured by the same approach as that of Example 1.

TABLE 3

| In a solution having a concentration of $1.0 \times 10^{-5}$ mol/l | |
|---|---|
| | Luminous wavelength |
| Compound No. A-1 | 431 nm |
| Comparative Compound 13 | 420 nm |
| Benzo[k]fluoranthene | 410 nm |

Figure 7:
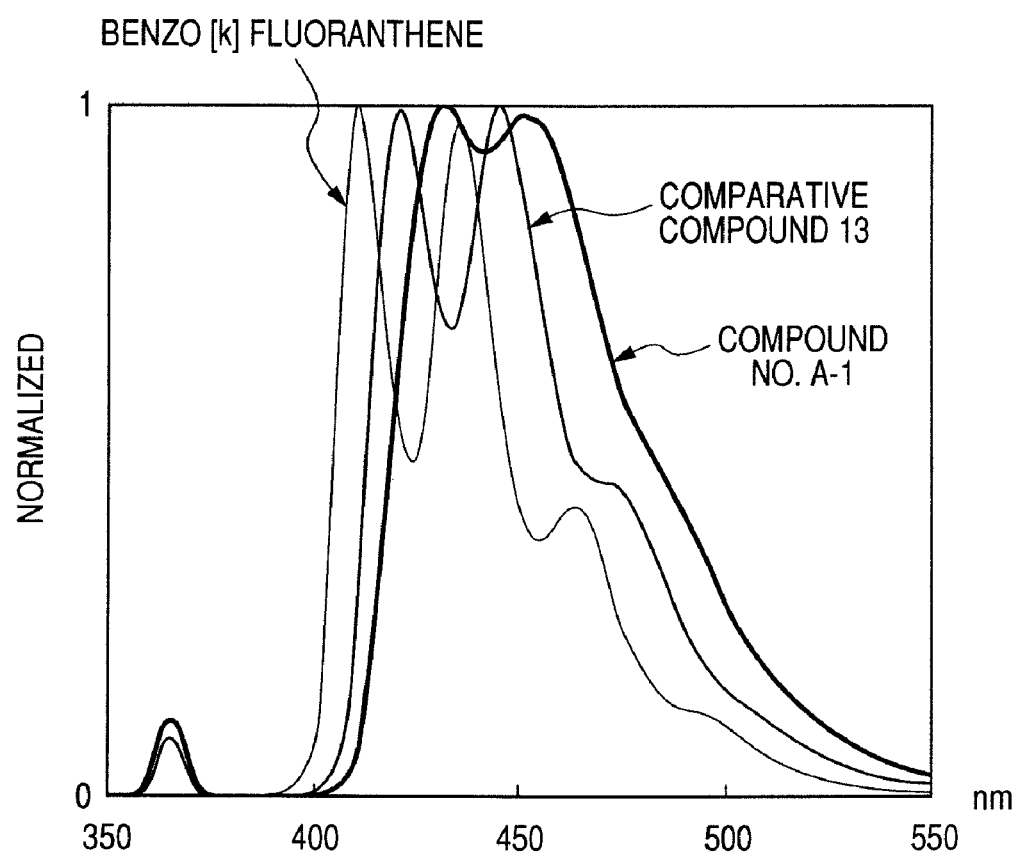
FIG. 7 is a view showing the emission spectrum of a solution of each of Compound No. A-1 of the present invention and Comparative Compound 13 in toluene having a concentration of $1\times10^{-5}$ mol/l.

FIG. 7 shows an emission spectrum in a solution.

The compound of the present invention has a luminous wavelength longer than that of each of Comparative Compound 13 and benzo[k]fluoranthene. Accordingly, the compound may be a blue light emitting compound having a wavelength appropriate for a light emitting device having high efficiency and good color purity when the compound is used in a display.

TABLE 4

| | Thin film | |
|---|---|---|
| | Luminous wavelength | Emission intensity |
| Compound No. A-1 | 449 nm | 1.93 |
| Comparative Compound 13 | 429 nm | 1.00 |
| Benzo[k]fluoranthene | No light emission | |

Figure 8:
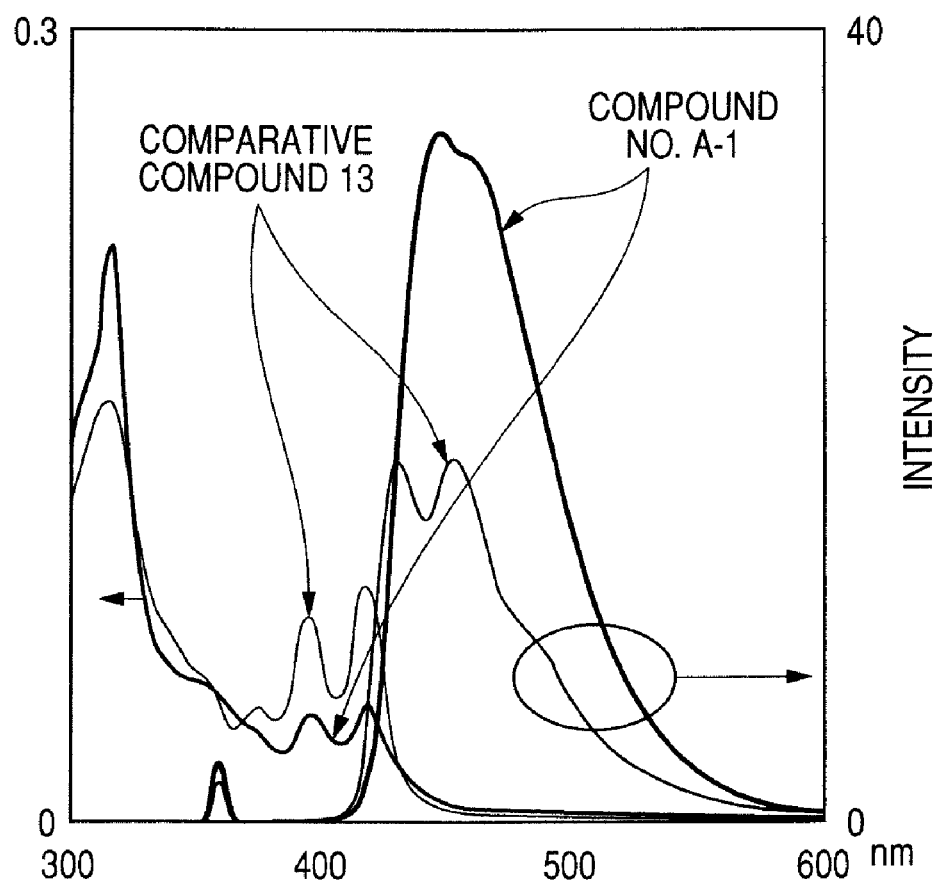
FIG. 8 is a view showing the emission spectrum and absorption spectrum of a thin film of each of Compound No. A-1 of the present invention and Comparative Compound 13 having a concentration of $1\times10^{-5}$ mol/l.

FIG. 8 shows an emission spectrum in a thin film. The emission intensities of two materials, that is, Compound No. A-1 and Comparative Compound 13 were compared by using a wavelength of 354 nm, represented by the point of intersection of the absorption curves of the materials at which the materials had the same absorbance, as an excitation wavelength. In addition, the thin film of benzo[k]fluoranthene was not observed to emit light.

When the compound of the present invention is used as a light emitting material in a light emitting device, the device is doped with the material at a concentration of about 0.1 to 20 wt % with respect to a host material. Accordingly, the light emitting properties of the light emitting material in a solid film are of extreme importance.

When the emission intensity of Comparative Compound 13 in a thin film is set to 1.0, Compound No. A-1 of the present invention has an emission intensity of 1.93: Compound No. A-1 has a quantum yield about twice as high as that of Comparative Compound 13.

In addition, each of the HOMO energy and LUMO energy of each of Compound No. A-1 and Comparative Compound 13 was measured by the same approach as that of Example 1.

TABLE 5

| | HOMO | LUMO |
|---|---|---|
| Compound No. A-1 | −5.89 eV | −2.98 eV |
| Comparative Compound 13 | −5.91 eV | −2.96 eV |

Compound No. A-1 of the present invention may have improved hole injecting property because the compound has HOMO energy larger than that of Comparative Compound 13. In addition, Compound No. A-1 may have improved electron injecting property as well because the compound has LUMO energy smaller than that of Comparative Compound 13. Accordingly, Compound No. A-1 may be a compound more appropriate for an electroluminescence device than Comparative Compound 13.

Example 2

As the anode, a film of indium tin oxide (ITO) having a thickness of 120 nm was formed on a glass substrate by a sputtering method, and the resultant was used as a transparent conductive supporting substrate. The resultant substrate was subjected to ultrasonic cleaning in acetone and isopropyl alcohol (IPA) in this order. Then, the substrate was washed in boiling IPA and dried. The substrate was further subjected to UV/ozone cleaning to be used as a transparent conductive supporting substrate.

A chloroform solution of a compound represented by Compound 14 shown below was formed into a film having a thickness of 20 nm by a spin coating method on the transparent conductive supporting substrate, whereby a hole transporting layer was formed.

Further, the following organic layers and electrode layers were continuously formed by vacuum deposition based on resistance heating in a vacuum chamber having a pressure of $10^{-5}$ Pa, whereby a device was produced.

Light emitting layer (20 nm): Exemplified Compound No. A-1 (2% in weight ratio): Compound 15
Electron transporting layer (30 nm): Bphen (manufactured by DOJINDO LABORATORIES)
Metal electrode layer 1 (0.5 nm): LiF
Metal electrode layer 2 (150 nm): Al Compound 14

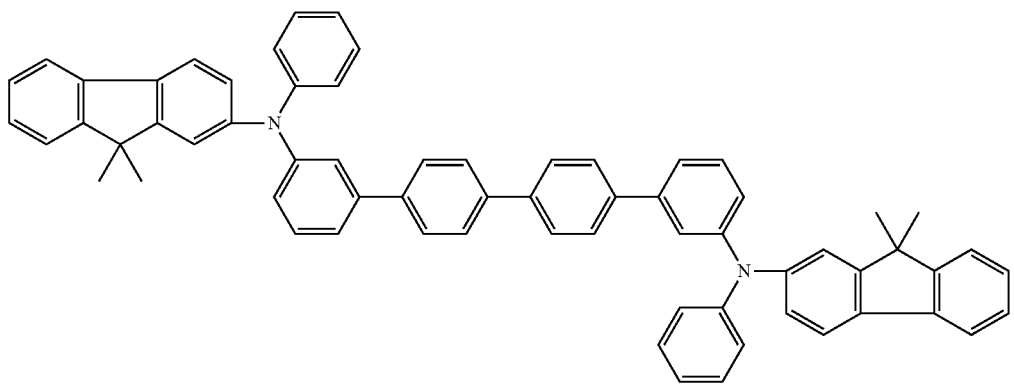

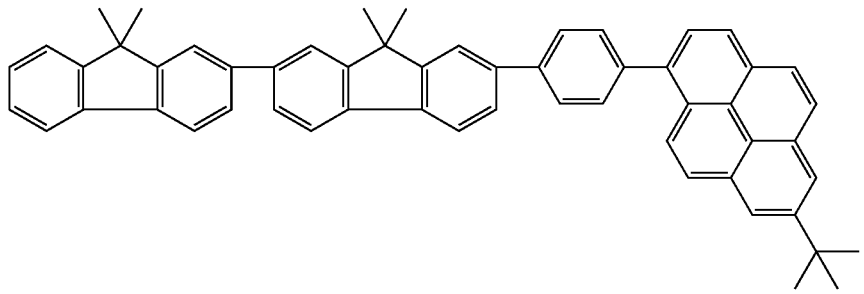

Compound 15

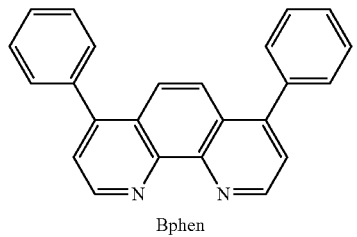

Bphen

The current-voltage characteristics of the resultant EL device were measured with a microammeter 4140 B manufactured by Hewlett-Packard Company, and the emission brightness of the device was measured with a BM 7 manufactured by TOPCON CORPORATION. The device of this example was observed to emit light with an emission brightness of 957 cd/m² and a luminous efficiency of 2.9 lm/W at an applied voltage of 4.5 V. In addition, the device was observed to emit blue light having CIE chromaticity coordinates (x, y) of (0.15, 0.10) and good color purity.

Further, a voltage was applied to the device for 100 hours under a nitrogen atmosphere. As a result, the device was observed to emit light in a favorable manner continuously.

Example 3

A device was produced in the same manner as in Example 2 except that Compound 16 was used instead of Compound 15 of Example 2. The device of this example was observed to emit light with an emission brightness of 980 cd/m² and a luminous efficiency of 2.7 lm/W at an applied voltage of 4.5 V. In addition, the device was observed to emit blue light having CIE chromaticity coordinates (x, y) of (0.15, 0.10) and good color purity.

Further, a voltage was applied to the device for 100 hours under a nitrogen atmosphere. As a result, the device was observed to emit light in a favorable manner continuously.

Compound 16

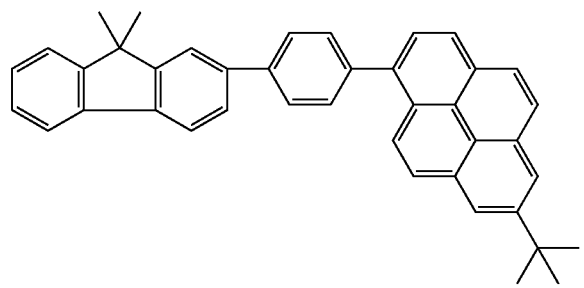

As can be seen from Examples 2 and 3, a light emitting device using a material having a skeleton obtained by combining a benzo[k]fluoranthene skeleton and a fluorene skeleton is excellent from the viewpoints of light emitting properties (a luminous wavelength and luminous efficiency), and heat stability. It has been also found that a light emitting device using the above guest and a material having a skeleton obtained by combining a pyrene skeleton and a fluorene skeleton as a host is excellent from the viewpoints of light emitting properties (a luminous wavelength and luminous efficiency), and durability.

Example 4

Synthesis of Exemplified Compound No. A-2

Exemplified Compound No. A-2 can be synthesized in the same manner as in Example 1 except that 2-iodo-9,9-diethylfluorene is used instead of 2-iodo-9,9-dimethylfluorene of Example 1.

Example 5

Synthesis of Exemplified Compound No. A-3

Exemplified Compound No. A-3 can be synthesized in the same manner as in Example 1 except that 2-iodo-9,9-diisoprophylfluorene is used instead of 2-iodo-9,9-dimethylfluorene of Example 1.

Example 6

Synthesis of Exemplified Compound No. A-54

Exemplified Compound No. A-54 was synthesized (15% synthesis yield) in the same manner as in Example 1 except that 3-bromofluoranthene was used instead of 2-iodo-9,9-dimethylfluorene of Example 1.

Matrix-assisted laser desorption/ionization time-of-flight mass spectrometry (MALDI-TOF MS) confirmed that the compound had an M+ of 652.2.

In addition, the structure of the compound was identified by NMR measurement.

$^1$H NMR(CDCl$_3$, 400 MHz) σ (ppm): 8.26 (dd, 2H, J=7.5 Hz), 8.09 (m, 2H), 8.02 (m, 4H), 7.91 (dd, 2H, J=15.7 Hz), 7.59 (m, 4H), 7.54-7.43 (m, 8H), 7.32 (m, 2H), 7.10 (t, 2H, J=8 Hz), 6.37 (d, 2H, J=7 Hz).

In addition, a dilute solution of the compound in toluene having a concentration of $1\times10^{-5}$ mol/l was prepared, and the emission spectrum of the solution was measured with a fluorescence spectrophotometer F-4500 manufactured by Hitachi, Ltd. The emission of blue light having good color purity and a narrow half width was observed; the light had a maximum luminous wavelength of 447 nm and a half width of 70 nm.

Example 7

Synthesis of Exemplified Compound No. A-55

Exemplified Compound No. A-55 can be synthesized in the same manner as in Example 1 except that bromopyrene is used instead of 2-iodo-9,9-dimethylfluorene of Example 1.

Example 8

Synthesis of Exemplified Compound No. A-56

Exemplified Compound No. A-56 can be synthesized in the same manner as in Example 1 except that 7-tertiary butyl-bromopyrene is used instead of 2-iodo-9,9-dimethylfluorene of Example 1.

Example 9

Synthesis of Exemplified Compound No. A-5

Exemplified Compound No. A-2 can be synthesized in the same manner as in Example 1 except that 2-iodo-7-tertiary butyl-9,9-dimethylfluorene is used instead of 2-iodo-9,9-dimethylfluorene of Example 1.

Example 10

Synthesis of Exemplified Compound No. A-44

Exemplified Compound No. A-44 can be synthesized in the same manner as in Example 1 except that Compound 17 is used instead of 2-iodo-9,9-dimethylfluorene of Example 1.

Compound 17

Example 11

An example of a method of producing a compound represented by the general formula (I) in which $R_7$ and $R_{12}$ are different and each represent substituents other than hydrogen atom is shown below.

Compound 6

Compound 18

Compound 19

Compound 20

In the formula, X represents a halogen atom. Compound 20 thus obtained is subjected to a reaction in the same manner as in the section (1-3) of Example 1, whereby a target product can be obtained.

Synthesis of Exemplified Compound No. A-20

Exemplified Compound No. A-20 can be synthesized by using bromobenzene and 2-iodo-9,9-dimethylfluorene as Compound 18 and Compound 19 in the above reaction formula, respectively.

Example 12

Synthesis of Exemplified Compound No. A-22

Exemplified Compound No. A-22 can be synthesized in the same manner as in Example 11 except that 3-bromotoluene is used instead of bromobenzene of Example 11.

Example 13

Synthesis of Exemplified Compound No. A-24

Exemplified Compound No. A-24 can be synthesized in the same manner as in Example 11 except that 2-bromobiphenyl is used instead of bromobenzene of Example 11.

Example 14

Synthesis of Exemplified Compound No. A-27

Exemplified Compound No. A-27 can be synthesized in the same manner as in Example 11 except that 1-bromonaphthalene is used instead of bromobenzene of Example 11.

Example 15

Synthesis of Exemplified Compound No. A-32

Exemplified Compound No. A-32 can be synthesized in the same manner as in Example 11 except that 5-bromophenanthrene is used instead of bromobenzene of Example 11.

Example 16

Synthesis of Exemplified Compound No. A-35

Exemplified Compound No. A-35 can be synthesized in the same manner as in Example 11 except that Compound 17 is used instead of bromobenzene of Example 11.

Example 17

A device was produced in the same manner as in Example 2 except that Compound 21 was used instead of Compound 15 of Example 2.

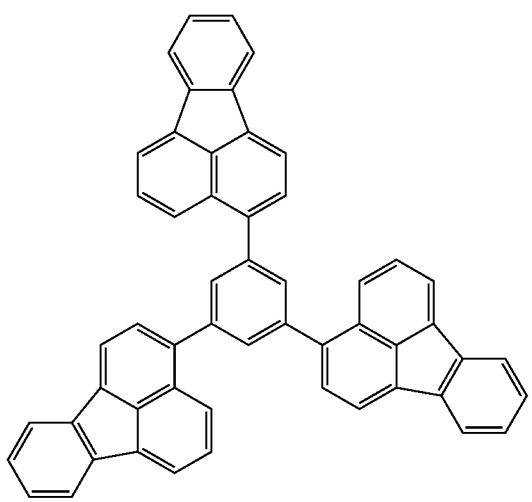

Compound 21

The device of this example was observed to emit blue light.

Example 18

Synthesis of Exemplified Compound No. A-70

Exemplified Compound No. A-70 was synthesized (9% synthesis yield) in the same manner as in Example 1 except that 2-bromo-9-methyl-9-trifluoromethylfluorene was used instead of 2-iodo-9,9-dimethylfluorene of Example 1.

Matrix-assisted laser desorption/ionization time-of-flight mass spectrometry (MALDI-TOF MS) confirmed that the compound had an M+ of 744.2.

In addition, the structure of the compound was identified by NMR measurement.

$^1$H NMR(CDCl$_3$, 400 MHz) σ (ppm): 8.07 (d, 2H, J=7.6 Hz), 7.92 (m, 2H), 7.88 (m, 2H), 7.78-7.65 (m, 8H), 7.56 (m, 2H), 7.46 (m, 4H), 7.26 (m, 2H), 6.69 (m, 2H), 1.83 (s, 3H), 1.82 (s, 3H).

In addition, a dilute solution of the compound in toluene having a concentration of 1×10$^{-5}$ mol/l was prepared, and the emission spectrum of the solution was measured with a fluorescence spectrophotometer F-4500 manufactured by Hitachi, Ltd. The emission of blue light having good color purity and a narrow half width was observed; the light had a maximum luminous wavelength of 448 nm and a half width of 61 nm.

Example 19

A device was produced in the same manner as in Example 2 except that Exemplified Compound No. A-54 was used instead of Exemplified Compound No. A-1 of Example 2. The device of this example was observed to emit light with an emission brightness of 130 cd/m$^2$ at an applied voltage of 4.5 V, and current efficiency and power efficiency were 4.0 cd/A and 2.7 lm/W, respectively. In addition, the device was observed to emit blue light having CIE chromaticity coordinates (x, y) of (0.15, 0.13) and good color purity.

Further, a voltage was applied to the device for 100 hours under a nitrogen atmosphere. As a result, the device was observed to emit light in a favorable manner continuously.

Example 20

A device was produced in the same manner as in Example 2 except that Exemplified Compound No. A-70 was used instead of Exemplified Compound No. A-1 of Example 2. The device of this example was observed to emit light with an emission brightness of 570 cd/m$^2$ at an applied voltage of 4.5 V, and current efficiency and power efficiency were 3.7 cd/A and 2.4 lm/W, respectively. In addition, the device was observed to emit blue light having CIE chromaticity coordinates (x, y) of (0.15, 0.09) and good color purity.

Further, a voltage was applied to the device for 100 hours under a nitrogen atmosphere. As a result, the device was observed to emit light in a favorable manner continuously.

Example 21

Synthesis of Exemplified Compound No. A-33

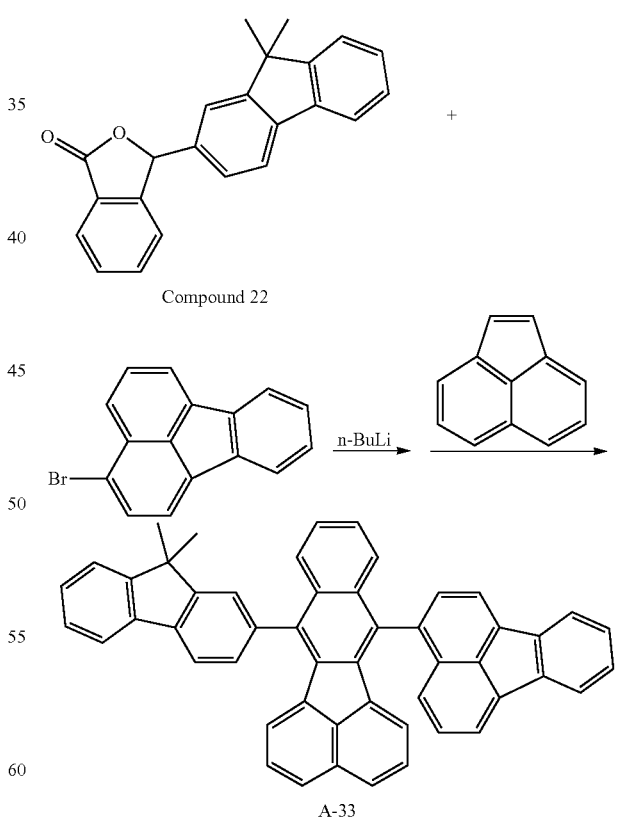

5.97 g (18.3 mmol) of 3-bromofluoranthene and 200 mL of diethyl ether were added to a 300 mL reaction vessel. The solution was cooled to −78° C., and 11.6 mL (18.3 mmol) of a solution of n-butyllithium in hexane having a concentration of 1.57 mol/L were added to the solution over 10 minutes. After the solution had been stirred at the temperature for 30 minutes, Compound 22 (5.15 g, 18.3 mmol) dissolved in 50 mL of diethyl ether was added to the solution in one stroke. The solution was heated to room temperature while a cooling bath was attached, and 100 mL of a 10% aqueous solution of ammonium chloride were added to the suspension, followed by extraction with ethyl acetate (100 mL×twice). An organic layer was collected, washed with distilled water and a saturated salt solution, and dried with anhydrous $MgSO_4$. After that, the solution was condensed and dried in a high vacuum, whereby a tan solid compound was obtained.

The resultant solid compound was loaded into a 500 mL reaction vessel, and 100 mL of xylene, 1.56 g (8.19 mol) of p-toluenesulfonic acid, and 4.17 g (27.4 mmol) of acenaphthylene were added to the vessel. The solution was vigorously stirred at 150° C. for 36 hours. Xylene was removed under reduced pressure, and 100 mL of saturated sodium bicarbonate water and 100 mL of distilled water were added to the solution, followed by extraction with chloroform (100 mL×twice). An organic layer was collected, washed with saturated sodium bicarbonate water, distilled water, and a saturated salt solution, and dried with anhydrous $MgSO_4$. After that, the desiccant was separated by filtration. After the filtrate was condensed, a black silica gel carrier was obtained. The carrier was purified by means of silica gel column chromatography (mobile phase; chloroform:hexane=1:3 to chloroform:hexane=1:1), whereby a reddish brown solid was obtained. The solid was suspended in a small amount of chloroform, and diethyl ether was added to the suspension to precipitate a crystal. The crystal was taken by filtration and purified by means of silica gel column chromatography (mobile phase; chloroform:hexane=1:3 to chloroform:hexane=1:2) again, whereby a reddish brown solid was obtained. The solid was suspended in a small amount of chloroform, and diethyl ether was added to the suspension, followed by filtration. After that, the resultant crystal was dried in a vacuum, and was then subjected to sublimation purification, whereby 2.5 g (3.88 mmol, 21% yield) of Exemplified Compound No. A-33 were obtained.

Matrix-assisted laser desorption/ionization time-of-flight mass spectrometry (MALDI-TOF MS) confirmed that the compound had an M+ of 644.3.

INDUSTRIAL APPLICABILITY

The compound represented by the general formula (I) of the present invention has a high glass transition temperature and high thin-film stability. Accordingly, the compound can be used as a guest for the light emitting layer of an organic light emitting device capable of emitting blue light with high brightness and good color purity at a low applied voltage.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-099896, filed Mar. 31, 2006, and 2006-334985, filed Dec. 12, 2006, which are hereby incorporated by reference herein in their entirety.

The invention claimed is:

1. A display comprising a substrate and an organic light emitting device, the organic light emitting device comprising a pair of electrodes formed of an anode and a cathode, and an organic compound layer interposed between the pair of electrodes, wherein the organic compound layer contains a compound, the compound being represented by the following general formula (I):

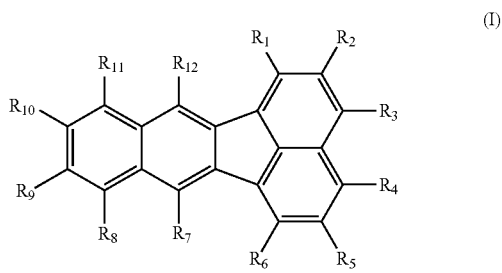

(I)

wherein $R_1$, $R_2$ and $R_5$ to $R_{12}$ each represent a hydrogen atom, a linear or branched alkyl group, a substituted or unsubstituted aryl group, or a substituted or unsubstituted heterocyclic group;

wherein $R_3$ and $R_4$ each represent a hydrogen atom, provided that at least one of $R_7$, $R_8$, and $R_9$ and at least one of $R_{10}$, $R_{11}$, and $R_{12}$ represent a substituted or unsubstituted condensed ring aromatic group, which is tricyclic or more; and wherein $R_7$ in the general formula (I) represents a substituted or unsubstituted fluoranthenyl group.

2. A display comprising an organic light emitting device, the organic light emitting device comprising a pair of electrodes formed of an anode and a cathode, and an organic compound layer interposed between the pair of electrodes, wherein the organic compound layer contains a compound, the compound being represented by the following general formula (IV):

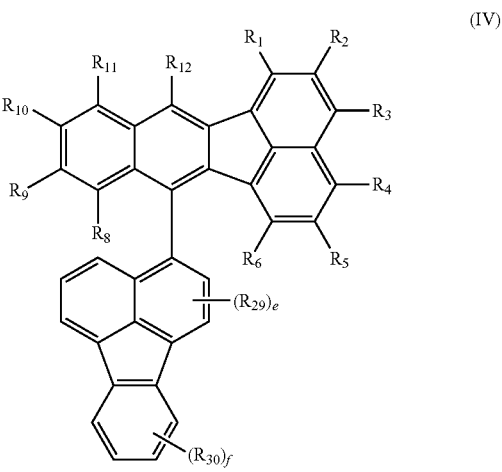

(IV)

wherein $R_1$, $R_2$, $R_5$, $R_6$, and $R_8$ to $R_{12}$ each represent a hydrogen atom, a linear or branched alkyl group, a substituted or unsubstituted aryl group, or a substituted or unsubstituted heterocyclic group;

wherein $R_3$ and $R_4$ each represent a hydrogen atom, provided that at least one of $R_{10}$, $R_{11}$, and $R_{12}$ represents a substituted or unsubstituted condensed ring aromatic group, which is tricyclic or more;

wherein $R_{29}$ and $R_{30}$ each represent a hydrogen atom, an alkyl group, a substituted or unsubstituted aryl group, a substituted or unsubstituted heterocyclic group, a substituted amino group, or a halogen atom;

wherein e represents an integer of 1 to 5, and f represents an integer of 1 to 4; and when the number of any one of $R_{29}$ and $R_{30}$ is two or more, $R_{29}$'s or $R_{30}$'s may be identical to or different from each other.

3. A display comprising an organic light emitting device, the organic light emitting device comprising a pair of electrodes formed of an anode and a cathode, and an organic compound layer interposed between the pair of electrodes, wherein the organic compound layer contains a compound, the compound being represented by the following general formula (V):

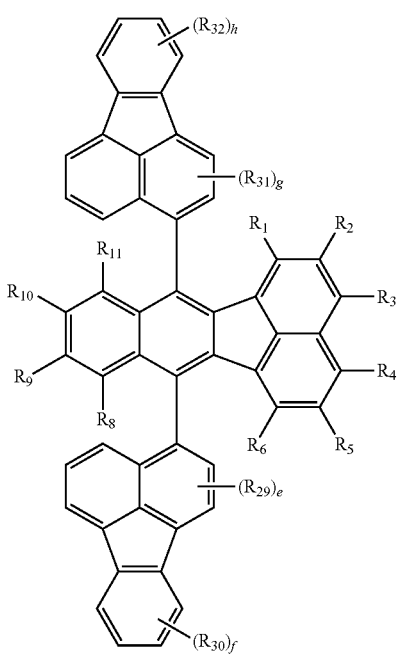

(V)

wherein $R_1$, $R_2$, $R_5$, $R_6$, and $R_8$ to $R_{11}$ each represent a hydrogen atom, a linear or branched alkyl group, a substituted or unsubstituted aryl group, or a substituted or unsubstituted heterocyclic group;

wherein $R_3$ and $R_4$ each represent a hydrogen atom;

wherein $R_{29}$ to $R_{32}$ each represent a hydrogen atom, an alkyl group, a substituted or unsubstituted aryl group, a substituted or unsubstituted heterocyclic group, a substituted amino group, or a halogen atom;

wherein e and g each represent an integer of 1 to 5, and f and h each represent an integer of 1 to 4; and when the number of any one of $R_{29}$, $R_{30}$, $R_{31}$, and $R_{32}$ is two or more, $R_{29}$'s, $R_{30}$'s, $R_{31}$'s, or $R_{32}$'s may be identical to or different from each other.

4. The display according to any one of claims 1-3, wherein the organic compound layer comprises a light emitting layer.

5. The display according to claim 4, wherein the light emitting layer is formed of at least two kinds of compounds including a host and a guest, and said guest is a compound represented by the general formula (I).

6. The display according to claim 4, wherein the light emitting layer is formed of at least two kinds of compounds including a host and a guest, and said guest is a compound represented by the general formula (IV).

7. The display according to claim 4, wherein the light emitting layer is formed of at least two kinds of compounds including a host and a guest, and said guest is a compound represented by the general formula (V).

8. The display according to claim 4, wherein the organic light emitting device emits a blue light.

* * * * *